United States Patent [19]

Berlin et al.

[11] Patent Number: 5,110,933

[45] Date of Patent: * May 5, 1992

[54] SALTS OF 3-AZABICYCLO(3.3.1) NONANES AS ANTIARRHYTHMIC AGENTS, AND PRECURSORS THEREOF

[75] Inventors: Kenneth D. Berlin, Stillwater; Benjamin J. Scherlag, Oklahoma City; Cyril R. Clarke, Stillwater; Surendra R. Otiv, Stillwater; Stan A. Zisman, Stillwater; Subbiah Sangiah, Stillwater; Satish V. Mulekar, Stillwater, all of Okla.

[73] Assignee: Board of Regents of Oklahoma State University, Stillwater, Okla.

[*] Notice: The portion of the term of this patent subsequent to Jan. 28, 2009 has been disclaimed.

[21] Appl. No.: 610,428

[22] Filed: Nov. 7, 1990

Related U.S. Application Data

[63] Continuation-in-part of Ser. No. 435,976, Nov. 13, 1989, Pat. No. 5,084,572.

[51] Int. Cl.$^5$ .................. C07D 495/08; C07D 495/10
[52] U.S. Cl. ................... 546/114; 546/112; 546/122
[58] Field of Search ......................... 546/114

[56] References Cited

U.S. PATENT DOCUMENTS 4,581,361  4/1986  Berlin et al. .................. 514/301

Primary Examiner—Alan L. Rotman
Attorney, Agent, or Firm—Head and Johnson

[57] ABSTRACT

Salts of 3-azabicyclo[3.3.1]nonanes are used in controlling antiarrhythmic processes and precursors thereof are disclosed.

4 Claims, No Drawings

SALTS OF 3-AZABICYCLO(3.3.1) NONANES AS ARTIARRHYTHMIC AGENTS, AND PRECURSORS THEREOF CROSS REFERENCE TO RELATED APPLICATION

This application is a continuation-in-part of Ser. No. 07/435,976 filed Nov. 13, 1989, now U.S. Pat. No. 5,084,572.

BACKGROUND OF THE INVENTION

1. Field of the Invention

This invention relates to antiarrhythmic compositions. Specifically, this invention relates to certain derivatives of 3-azabicyclo[3.3.1]nonanes.

2. Description of the Prior Art

3-Azabicyclo[3.3.1]nonanes with heteroatoms such as N, S, and O at the 7-position are known and documented in the chemical literature. A review in Chemical Reviews, Volume 81, No. 2, pages 149-174 (1981), entitled "Chemistry of 3-Azabicyclo[3.3.1]nonanes" by R. Jeyaraman and S. Avila, covers the synthesis, reactions and stereochemistry of the title compounds. The review acknowledges the close resemblance of 3-azabicyclo[3.3.1]nonanes (3-ABN) to aza- and diazaadamantanes in conformation and stereochemistry, and this has caused progress in the chemistry of the title compounds. The review further acknowledges that 3-ABN systems can be obtained by a Mannich, or modified Mannich, reaction involving a condensation of ketones or aldehydes with a primary amine under relatively mild conditions. Thus, the availability of a variety of ketones or aldehydes has prompted studies on 3-ABNs.

According to the chemical literature, a few derivatives of 3-ABN have exhibited useful biological properties. Potent analgesic and antitusive characteristics as well as antagonism to analgesic effects and to narcotic action have been observed, depending upon the groups attached to the basic structure. In addition, some examples have displayed sedative action as well as antipyretic and hypoglycemic activity. Simple 3-ABN has been reported to be effective against influenza infection. Some derivatives have recorded antiarrhythmic properties. Certain sulfur-substituted, as well as selenium-substituted examples, have been reported as accessible via a Mannich reaction or a modified Mannich reaction. In U.S. Pat. No. 4,581,361 and U.S. Pat. No. 4,778,892, for example, such materials are disclosed and claimed as antiarrhythmic agents.

SUMMARY OF THE INVENTION

The present invention involves novel derivatives of 3-azabicyclo[3.3.1]nonanes having the basic formula:

$$Y \underset{Q}{\overset{Z}{\diagup\diagdown}} N-R \cdot HX$$

$X = ClO_4, Br, Cl, HSO_4,$ citrate, fumarate

| Y | Z | R | Q | Number |
|---|---|---|---|---|
| PhC(O)N | $CH_2$ | $(H_3C)_2CH$ | $CH_2$ | (1) |
| 4-ClC$_6$H$_4$C(O)N | $CH_2$ | $(H_3C)_2CH$ | $CH_2$ | (2) |
| 3,4-(H$_3$CO)$_2$C$_6$H$_3$C(O)N | $CH_2$ | $(H_3C)_2CH$ | $CH_2$ | (3) |
| 3,4,5-(H$_3$CO)$_3$C$_6$H$_2$C(O)N | $CH_2$ | $(H_3C)_2CH$ | $CH_2$ | (4) |
| PhCH$_2$N | $CH_2$ | $(H_3C)_2CH$ | $CH_2$ | (5) |
| 4-ClC$_6$H$_4$CH$_2$N | $CH_2$ | $(H_3C)_2CH$ | $CH_2$ | (6) |
| 3,4-(H$_3$CO)$_2$C$_6$H$_3$CH$_2$N | $CH_2$ | $(H_3C)_2CH$ | $CH_2$ | (7) |
| S | $CH_2$ | $(H_3C)_2CH$ | $CH_2$ | (8) |
| S | $CH_2$ | 3-I-C$_6$H$_4$CH$_2$ | $CH_2$ | (9) |
| S $\rightarrow$ O | $CH_2$ | PhCH$_2$ | $CH_2$ | (10) |
| S | C(OCH$_3$)$_2$ | PhCH$_2$ | $CH_2$ | (11) |
| PhCH$_2$N | C(OCH$_3$)$_2$ | PhCH$_2$ | $CH_2$ | (12) |
| C$_2$H$_5$O(O)C | $CH_2$ | PhCH$_2$ | $CH_2$ | (13) |
| C$_2$H$_5$O(O)C | S–C–S (cyclic) | PhCH$_2$ | $CH_2$ | (14) |
| S | $CH_2$ | PhC(O) | $CH_2$ | (15) |
| S $\rightarrow$ O | C(OCH$_3$)$_2$ | PhCH$_2$ | $CH_2$ | (16) |
| PhCH$_2$N | $CH_2$ | PhCH$_2$ | C=O | (17) |

The present invention also provides for novel intermediates of the class of 3-azabicyclo[3.3.1]nonan-9-ones having the formula:

$$Y \diagup\diagdown =O \quad N-R$$

| Y | R | Number |
|---|---|---|
| S | CH$_2$Ph | (18) |
| NCH$_2$Ph | CH$_2$Ph | (19) |
| CHCO$_2$Et | CH$_2$Ph | (20) |
| NCH(CH$_3$)$_2$ | CH$_2$Ph | (21) |
| NCH(CH$_3$)$_2$ | CH$_2$C$_6$H$_4$-4-Cl | (22) |
| NCH(CH$_3$)$_2$ | CH$_2$C$_6$H$_3$-3,4-(OCH$_3$)$_2$ | (23) |

-continued

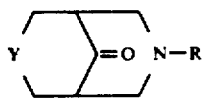

| Y | R | Number |
|---|---|---|
| NCH(CH$_3$)$_2$ | CH$_2$C$_6$H$_2$-3,4,5-(OCH$_3$)$_3$ | (24) |
| S | CH$_2$C$_6$H$_4$-3-I | (25) |
| S | CH(CH$_3$)$_2$ | (26) |

The invention further provides additional 3-azabicyclo[3.3.1]nonanes of the formula:

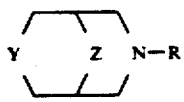

| Y | Z | R | Number |
|---|---|---|---|
| S | CH$_2$ | CH$_2$Ph | (27) |
| S | CH$_2$ | H | (28) |
| S | CH$_2$ | C(O)Ph | (29) |
| NCH(CH$_3$)$_2$ | CH$_2$ | CH$_2$Ph | (30) |
| NCH(CH$_3$)$_2$ | CH$_2$ | H | (31) |
| NCH(CH$_3$)$_2$ | CH$_2$ | C(O)Ph | (32) |
| NCH(CH$_3$)$_2$ | CH$_2$ | C(O)—C$_6$H$_4$-4-Cl | (33) |
| NCH(CH$_3$)$_2$ | CH$_2$ | C(O)C$_6$H$_3$-3,4-(OCH$_3$)$_2$ | (34) |
| NCH(CH$_3$)$_2$ | CH$_2$ | C(O)C$_6$H$_2$-3,4,5-(OCH$_3$)$_2$ | (35) |
| NCH(CH$_3$)$_2$ | CH$_2$ | S(O)$_2$Ph | (36) |
| NCH$_2$Ph | CH$_2$ | CH$_2$Ph | (37) |
| CHCO$_2$Et | CH$_2$ | 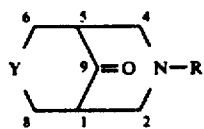 | (38) |

Specifically, the invention relates to the above salts (1)–(17) of certain 3-azabicyclo[3.3.1]nonanes and precursors (18)–(38) as used in controlling antiarrhythmic processes. Thus, it is the object of the present invention to provide novel compositions that display biological activity. Fulfillment of this object and the presence and fulfillment of other objects will be apparent upon complete reading of the specifications and claims.

DESCRIPTION OF THE PREFERRED EMBODIMENTS

The chemical compositions according to the preferred embodiments of this invention are heteronuclear ring organic compounds based on the 3-azabicyclo[3.3.1]nonane structures as follows:

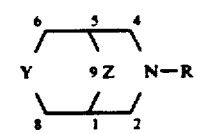
(39)

(40)

-continued (41)

Wherein the 3-position in general structures (39-41) is nitrogen [as specifically in (1-38)], the 7-position includes nitrogen [as specifically in (1-7), (12), (17), (19), (21-24), and (30-37)], sulfur [as specifically in (8-11), (15), (16), (18), and (25-29)], and carbon [as specifically in (13), (14), (20), and (38)]. With nitrogen in the 3- or 7-position, a N—C bond is always present except for (28) and (31) which have N—H bonds and (36) which has an N—S bond. The 9-position can be preferably unsubstituted [as specifically in (1)–(10), (13), (15), (17), and (27)–(38)], 9-one [as specifically in (18)–(26)], 9,9-dimethoxy [as specifically in (11), (12), and (16)], or a 1,3-dithiolane [as specifically in (14) and (38)]. The alkylated nitrogen atom at the 3-position [as specifically in (1)–(16)] and their corresponding tertiary amine acid salts [hydroperchlorate, HCl, HBr, H$_2$SO$_4$, citrate, and fumarate] are included along with a system containing an alkylated nitrogen at the 7-position as in (17) and the corresponding salts.

These compounds are the active ingredients for potential drugs and/or intermediates for the active ingredients of potential drugs to use in the treatment of disorders of the heart. They exhibit good activity in animal models and as such are viable candidates to control life-threatening arrhythmias found in humans who experience heart attacks or major infarctions of the heart.

Typically, the 9-one systems shown by the general formula (39) [as specifically in (18)–(26)] are synthesized by the reaction of a tetrahydro-4-heteracyclohexanone in the presence of an aldehyde and amine or ammonium salt in accordance with a Mannich or Mannich type reaction. For example, and as illustrated in the following reaction scheme A, 1-isopropyl-4-piperidinone (42) [or 1-benzyl-4-piperidinone (43) or 4-thianone (44)] was allowed to react with benzylamine, 4-chlorobenzylamine, 3,4-dimethoxybenzylamine, 3,4,5-trimethoxybenzylamine, and the like with paraformaldehyde in the presence of acetic acid/methanol to produce the 3-azabicyclo[3.3.1]nonan-9-ones (39) [representative examples are (18), (19), and (21)–(24)]. The ketone (39) is then reduced with hydrazine hydrate in triethylene glycol/potassium hydroxide media to give members of (40) which could be reacted with perchloric acid, hydrochloric acid, hydrobromic acid, sulfuric acid, citric acid, or fumaric acid in benzene, ether, and/or isopropyl alcohol to yield the corresponding hydroperchlorate, hydrochloride, hydrosulfate, citrate, or fumarate derivative (41). Related examples where Y is benzyl or sulfur follow similarly. Thus the method is applicable to obtain members of (18)–(26), with the exception of (20) which was prepared from

REACTION SCHEME A

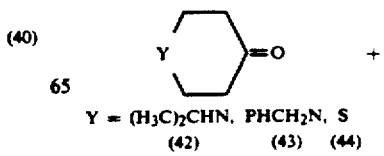

Y = (H$_3$C)$_2$CHN, PHCH$_2$N, S
(42) (43) (44)

REACTION SCHEME A

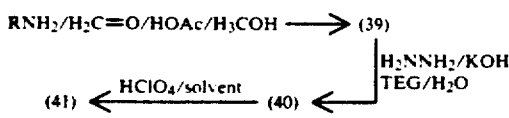

the enamine in scheme B starting from (43). The co-reactant with (43) to give (20) is made by

REACTION SCHEME B

(43) + pyrrolidine/C₆H₆/distill ⟶

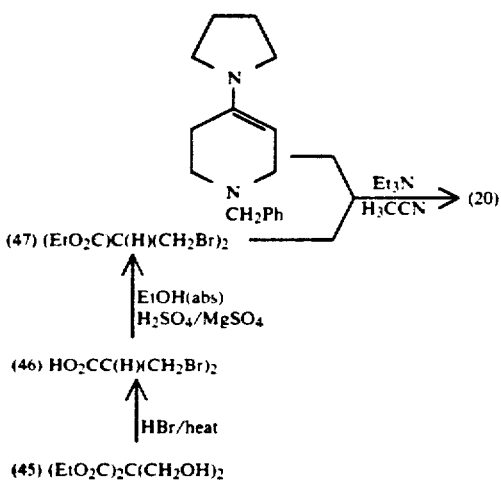

treatment of ester (45) with hydrobromic acid to give acid (46) under standard conditions. Esterification of (46) under the usual conditions produced dibromide (47) which was condensed with the enamine in the presence of triethylamine in acetonitrile to yield ketone (20) under the usual conditions.

Reduction of the ketones in scheme A, including ketone (20), via Wolff-Kishner conditions, as illustrated with hydrazine/KOH in triethylene glycol, leads to amines of general formula (40) [specifically (27), (30), and (37) are representative examples]. Addition of perchloric acid [or HCl, HBr, H₂SO₄, citric acid, or fumaric acid] in benzene or isopropyl alcohol gives members of general formula (41) [(5)–(9), and (13) are representative examples].

In reaction scheme C, members of (40) [representative examples are (28), (29), (31), and (32)–(36)] were obtained as outlined. Specific members of the family of (40) with an N—H bond [note these examples are representative starting materials for the amide systems], namely (28) and

REACTION SCHEME C

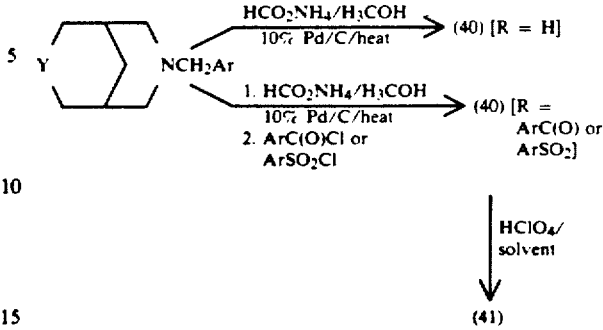

(31) as representative examples, are isolable directly from the reaction mixture after workup. Direct aroylation or sulfonation of these types of intermediates (40) in a two-phase system under modified Schotten-Baumann conditions, or phase transfer conditions, leads to amide members of (39) [(29), (32)–(35), and (36) are representative examples]. Treatment of these latter amide members of (40), such as (32)–(35) and related systems, with perchloric acid, HCl, HBr, H₂SO₄, citric acid, or fumaric acid in benzene, ether, and/or isopropyl alcohol produces salts (41) illustrated by (1)–(4) as representative examples.

Ketal formation from members of (39), using methanol or 1,2-ethanedithiol, under standard conditions, produced members of (40), such as illustrated with (38) as a representative example, or, after treatment with perchloric acid, HCl, HBr, H₂SO₄, citric or fumaric acid, produced members of (41) such as illustrated with (11), (12), (14), and (16) as representative examples.

Since oxidation products are viable candidates as potential metabolites from use of these compounds in animals, including humans, oxidation of specific sites was performed. As an example, oxidation of (37) illustrates the introduction of an oxygen atom alpha to the nitrogen when treated with RuO₂xH₂O/NaIO₄ in a water/carbon tetrachloride mixture to produce lactam (17). Moreover, oxidation of sulfur to give members of (41), with sulfoxides (10) and (16) as representative examples, can lead to potential metabolites. Salt formation is again effected by the method outlined previously for members of (41).

EXAMPLE I

7-Benzyl-3-thia-7-azabicyclo[3.3.1]nonan-9-one (18)

Ketone (18) was prepared by the method in U.S. Pat. No. 4,581,361.

EXAMPLE II

7-Benzyl-3-thia-7-azabicyclo[3.3.1]nonane (27)

This amine (27) was prepared from ketone (18) by the method of Bailey, III, et. al. J. Med. Chem., vol. 27(6) pp. 758–767 (1984).

EXAMPLE III

7-Benzyl-3-thia-7-azabicyclo[3.3.1]nonane Hydroperchlorate (48)

This amine salt was prepared from amine (27) by the method of Bailey, III, et. al. J. Med. Chem., vol. 27(6) pp. 758–767 (1984).

EXAMPLE IV

3-Thia-7-azabicyclo[3.3.1]nonane (28)

A 50-mL, three-necked, round-bottomed flask was equipped with a magnetic stirrer, a heating mantle, a standard condenser with a $N_2$ inlet and two glass stoppers. In one portion, anhydrous $HCO_2NH_4$ (1.11 g, 17.1 mmol) was added under $N_2$ to a mixture of the amine (27, 0.90 g, 3.86 mmol) and 10% Pd/C (0.90 g) in anhydrous $CH_3OH$ (25 mL). With stirring, the mixture was brought to reflux for 30 min, filtered through a Celite pad on a fritted funnel (which was washed thoroughly with $CH_2Cl_2$), and then concentrated to give a gummy oil with suspended solid. This material was again dissolved in $CH_2Cl_2$ (~15 mL), and the suspension was filtered to remove any unreacted ammonium formate. The filtrate was then concentrated to near saturation and placed in a diffusion chamber of ether overnight. Crude amine (28) became an oil; however, the mother liquor, containing predominantly starting material, could be decanted. Chromatography of the oil employed a gradient elution of $CH_3OH/CH_2Cl_2$ (300 mL of 10% $CH_3OH/CH_2Cl_2$, 50 mL of 20% $CH_3OH/CH_2Cl_2$, 100 mL of 50% $CH_3OH/CH_2Cl_2$, and 100 mL of $CH_3OH$) on silica gel (35 g, 1.5 cm × 62 cm) and afforded 0.32 g (56.9%) of amine (28) ($R_f$=0.11, 10% $CH_3OH/CH_2Cl_2$) as a light, gummy solid which was used without further purification. $^1H$ NMR ($DCCl_3$) δ1.84, 2.04 [two bd, 2H, H(9)], 2.31 [bs, 2H, H(1,5)], 2.80 [bd, 2H, H(2,4)$_{ax}$, J=12.3 Hz], 3.20 [bd, 2H, H(2,4)$_{eq}$, J=13.7 Hz], 3.45 [m, 2H, H(6,8)$_{ax}$], 3.73 [bd, 2H, H(6,8)$_{eq}$, J=13.2 Hz], 7.59 (bs, 1H, N-H); $^{13}C$ NMR ($DCCl_3$) ppm 24.88 [d, C(1,5)], 29.79 [t, C(9)], 32.17 [t, C(2,4)], 47.8 [t, C(6,8)].

EXAMPLE V

7-Benzoyl-3-thia-7-azabicyclo[3.3.1]nonane (29)

A 10-mL, two-necked, round-bottomed flask was equipped with a magnetic stirrer, an ice bath, a standard condenser with a $N_2$ inlet, and a glass stopper. To a chilled (5° C.) solution of NaOH pellets (0.1 g, 2.38 mmol) in $H_2O$ (1.7 mL) was added a solution of the amine (28, 0.17 g, 1.19 mmol) in $CH_2Cl_2$ (1 mL). This was followed by the dropwise addition of a solution of benzoyl chloride (0.2 g, 1.43 mmol) over ~5 min. After stirring for 30 min at 0°-5° C., 30 min at RT, and then 15 min over a steam bath, the mixture was diluted with $H_2O$ (15 mL), and the mixture was extracted ($CH_2Cl_2$, 3×15 mL). Combining the extracts, drying ($Na_2SO_4$, overnight), filtering, and concentrating the solution gave a viscous yellow oil. Chromatography of the oil on alumina (38 g, 2.4 cm × 17 cm) employed ethyl acetate as eluant and afforded amide (29) ($R_f$=0.47) as white crystals (157 mg, 53.3%); mp 95°-96° C. IR (KBr) cm$^{-1}$ 3065, 3045 (Ar C—H), 3000, 2985, 2940, 2910, 2855, 2835 (C—H), 1635 (C=O), 745, 720 (C—H out of plane, mono); $^1H$ NMR ($DCCl_3$) δ1.78-1.93 [m, 3H, H(9) and H(1)], 2.15 [bs, 1H, H(5)], 2.39 [d, 1H, H(4)$_{ax}$, J=13.9 Hz], 2.77 [d, 1H, H(6)$_{ax}$, J=12.3 Hz], 3.12-3.21 [m, 3H, H(4)$_{eq}$ and H(6)$_{eq}$], 3.41 [d, 1H, H(2)$_{ax}$, J=12.8 Hz], 3.89 [d, 1H, H(2)$_{eq}$, J=13.4 Hz], 4.98 [d, 1H, H(8)$_{eq}$, J=13.1 Hz], 7.38-7.44 [m, 5H, Ar—H]; $^{13}C$ NMR ($DCCl_3$) ppm 26.53 [C(1)], 26.87 [C(5)], 31.73 [C(2)], 31.78 [C(9)], 32.34 [C(4)], 46.07 [C(8)], 52.12 [C(6)], 126.46, 128.41, 128.83, 137.35 (Ar—C), 170.38 [C=O]. Anal. Calcd. for $C_{14}H_{17}NOS$: C, 67.98; H, 6.93. Found: C, 68.01; H, 7.07.

EXAMPLE VI

7-Benzyl-3-isopropyl-3,7-diazabicyclo[3.3.1]nonan-9-one (21)

A 500-mL, three-necked, round-bottomed flask was equipped with a magnetic stirrer, a heating mantle, a 250-mL addition funnel, a standard condenser with a $N_2$ inlet and a glass stopper. A mixture of benzylamine (10.71 g, 100 mmol), HCl (37%, 9.86 g, 100 mmol), glacial acetic acid (3.0 g, 50 mmol) and paraformaldehyde (6.31 g, 210 mmol) in deoxygenated ($N_2$ bubbled in for 1 h) $CH_3OH$ (100 mL) was stirred at reflux for 15 min under $N_2$. A solution of 1-isopropyl-4-piperidinone (42, 14.12 g, 100 mmol) and glacial acetic acid (6.0 g, 100 mmol) in $CH_3OH$ (100 mL) was then added dropwise to the mixture over 30 min, followed by stirring at reflux for an additional 18.5 h. Concentration of the solution gave an oil which was redissolved in $H_2O$ (100 mL). An ether extract (100 mL) of this acidic solution was discarded. Basicification (pH~13) of the water layer was achieved by the addition of 10% NaOH, resulting in the formation of a milky suspension which was extracted (ether, 4×60 mL). Combined extracts were dried ($Na_2SO_4$, 1 h), filtered, and concentrated to a viscous red oil, which, when distilled (175°-185° C./10$^{-5}$ mm Hg), afforded a light yellow oil (15.6 g, 57.2%) that solidified when refrigerated at −10° C.; mp 46°-47.5° C. This solid could be recrystallized (pentane) to give an analytical sample of ketone (21); mp 49°-50° C. IR (KBr) cm$^{-1}$ 3095, 3070, 3035 (Ar—H), 2975, 2900, 2820 (C—H), 1745 (C=O), 1605, 1495 (C=C), 740, 700 (C—H out of plane, mono); $^1H$ NMR ($DCCl_3$) δ1.02 (d, 6H, $CH_3$), 2.58 [bs, 2H, H(1,5)], 2.87 [m, 5H, ring protons and $CH(CH_3)_2$], 3.03 (dd, 4H, ring protons), 3.53 (s, 2H, $ArCH_2$), 7.30 (m, 5H, Ar—H); $^{13}C$ NMR ($DCCl_3$) ppm 18.25 ($CH_3$), 46.93 [C(1,5)], 53.41 [$CH(CH_3)_2$], 53.71 [C(2,4)], 58.07 [C(6,8)], 61.25 ($ArCH_2$), 127.09, 128.25, 128.69, 138.67 (Ar—C), 215.20 (C=O); $^{15}N$ NMR ($DCCl_3$) ppm 39.25 [N(7)], 40.80 [N(3)]. Anal. Calcd. for $C_{17}H_{24}N_2O$: C, 74.96; H, 8.88; N, 10.28. Found: C, 75.18; H, 8.61; N, 10.24.

EXAMPLE VII

7-Benzyl-3-isopropyl-3,7-diazabicyclo[3.3.1]nonane (30)

To a mixture of KOH pellets (85%, 11.62 g, 176 mmol) and the ketone (21) (6.0 g, 22 mmol) in triethylene glycol (100 mL) was added hydrazine (95%, 2.97 g, 88 mmol) in one portion in a 200-mL, jacketed flask equipped with a magnetic stirrer, a heating mantle, a standard condenser, a lower take-off condenser with a $N_2$ inlet, and two glass stoppers. A heating temperature of 200°-210° C. for 4 h under $N_2$ was produced by boiling tetralin (bp 207° C.) in the jacket. Cooling of the solution to RT was followed by the addition of chilled water (125 mL). Combined extracts (ether, 4×50 mL) of the suspension were washed with 10% NaOH (50 mL) and saturated NaCl (50 mL), dried ($Na_2SO_4$, 1 h), filtered, and concentrated (rotary evaporator then vacuum pump, overnight, RT/0.2 mm Hg) to a yellow oil (5.53 g, 97.3%). Analysis of the very slight crude amine (30) showed no carbonyl stretch in the IR spectrum, and thus it was used without further purification.

EXAMPLE VIII

7-Benzyl-3-isopropyl-3,7-diazabicyclo[3.3.1]nonane Hydroperchlorate (5)

A 125-mL Erlenmeyer flask was equipped with a magnetic stirrer and an ice bath. To a stirred, chilled (5° C.) solution of the amine (30, 0.84 g, 3.25 mmol) in dry ether (50 mL) was added dropwise a solution of $HClO_4$ (60%, 1.08 g, 6.50 mmol) in isopropyl alcohol (3 mL) over 20 min. After the mixture was stirred an additional hour, a white powdery material was filtered, and then dissolved in $CH_3OH$. Decolorizing with Norit, filtering, and concentrating the solution gave a solid that was recrystallized ($CH_3OH$) to give 0.65 g (49.4%) of salt (5); mp 152.0°-152.5° C. IR (KBr) cm$^{-1}$ 3050, 3030 (Ar C—H), 2970, 2940, 2910, 2810 (C—H), 1090 (Cl—O); $^1$H NMR (DMSO-d$_6$) δ1.18 (d, 6H, $CH_3$), 1.62 [d, 1H, H(9), J = 12.4 Hz], 1.82 [d, 1H, H(9), J = 12.7 Hz], 2.14 [bs, 2H, H(1,5)], 2.47 [d, 2H, H(6,8)$_{ax}$, J = 11.4 Hz], 3.11 [m, 4H, H(2,4)$_{ax}$ and H(6,8)$_{eq}$], 3.32 [d, 2H, H(2,4)$_{eq}$, J = 11.8 Hz], 3.47 [h, 1H, $CH(CH_3)_2$], 3.52 (s, 2H, ArCH$_2$), 7.30–7.46 (m, 5H, Ar—H); $^{13}$C NMR (DMSO-d$_6$) ppm 16.11 (q, $CH_3$), 27.24 [d, C(1,5)], 29.67 [t, C(9)], 52.85 [t, C(2,4[, 56.00 [d, $CH(CH_3)_2$], 56.85 [t, C(6,8)], 61.15 (t, ArCH$_2$), 127.65, 128.35, 129.38, 136.35 (Ar—C); $^{15}$N NMR (DMSO-d$_6$) ppm 50.90 [N(7)], 60.47 [N(3)]. Anal. Calcd. for $C_{17}H_{27}ClN_2O_4$: C, 56.90; H, 7.58; N, 7.81. Found: C, 56.70; H, 7.45; N, 7.84.

EXAMPLE IX

3-Isopropyl-3,7-diazabicyclo[3.3.1]nonane (31)

A 200-mL, three-necked, round-bottomed flask was equipped with a magnetic stirrer, a heating mantle, a condenser with a N$_2$ inlet, and two glass stoppers. To a stirred mixture of amine (30) (5.53 g, 21.4 mmol) and 10% Pd/C (0.64 g, 30 mg/mmol of amine) in $CH_3OH$ (80 mL) was added anhydrous $HCO_2NH_4$ (3.37 g, 53.5 mmol) in one portion. Stirring the mixture at reflux under N$_2$ for 30 min, cooling the new mixture to RT, and filtering through a celite pad was followed by concentration of the resulting solution to give a viscous oil. The oil was then dissolved in H$_2$O (80 mL) and the pH was adjusted to ~12 by the addition of 10% NaOH. Combined extracts ($CH_2Cl_2$, 4×40 mL) of the aqueous solution were dried, filtered, and concentrated (rotary evaporator then vacuum pump, 10 min, RT/0.2 mm Hg) to give amine (31) as a light oil (3.35 g, 93.0%) which was used without further purification. IR (film) cm$^{-1}$ 3315 (N—H), 2965, 2900, 2850, 2790, 2760, 2725 (C—H); $^1$H NMR (DCCl$_3$) δ1.01 (d, 6H, $CH_3$, J = 6.7 Hz), 1.60–1.67 [m, 3H, H(1,5) and H(9)], 2.53–2.59 [m, 3H, ring protons and $CH(CH_3)_2$], 2.90–3.06 [m, 6H, ring protons], 3.56 (bs, 1H, N—H); $^{13}$C NMR (DCCl$_3$) ppm 18.12 ($CH_3$), 30.04 [C(1,5)], 33.62 [C(9)], 52.86 [C(6,8)], 54.59 [$CH(CH_3)_2$], 54.65 [C(2,4)].

EXAMPLE X

3-Benzoyl-7-isopropyl-3,7-diazabicyclo[3.3.1]nonane (32)

A three-necked, 50-mL, round-bottomed flask was equipped with a magnetic stirrer, an ice bath, a standard condenser with a N$_2$ inlet, and two glass stoppers. To a solution of 10% NaOH (8.94 g, 22.3 mmol) was added the amine (31, 1.14 g, 6.77 mmol) in $CH_2Cl_2$ (15 mL) in one portion. Dropwise addition of a solution of benzoyl chloride (1.05 g, 7.45 mmol) in $CH_2Cl_2$ (5 mL) to the mixture over 15 min under N$_2$ was followed by stirring an additional 2.75 h at RT. After the addition of H$_2$O (30 mL), the organic layer was separated. Additional extracts ($CH_2Cl_2$, 3×25 mL) were combined with the initial organic layer, dried (Na$_2$SO$_4$, 1 h), filtered, and concentrated (aspirator followed by vacuum pump, 1 h, RT/0.2 mm Hg) to give an orange oil. Chromatography of the oil was performed over neutral alumina (200 g, 2.1 cm×33 cm) with ethyl acetate as eluant. Fractions (R$_f$=0.70) were combined and concentrated (rotary evaporator then vacuum pump, overnight, RT/0.2 mm Hg) to yield 1.52 g (82.4%) of the amide (32) as an oil which was used without further purification. IR (film) cm$^{-1}$ 3085, 3065, 3035 (Ar C—H), 2970, 2925, 2865, 2805, 2780, 2750 (C—H), 1635 (C=O), 730, 710 (C—H out of plane, mono); $^1$H NMR (DCCl$_3$) δ0.96 (d, 3H, $CH_3$, J = 6.4 Hz), 1.07 (d, 3H, $CH_3$, J = 6.6 Hz), 1.65–1.78, [m, 3H, H(5) and H(9)], 1.97 [bs, 1H, H(1)], 2.41 [d, 1H, H(4)$_{ax}$, J = 10.3 Hz], 2.50 [d, 1H, H(6)$_{ax}$, J = 11.0 Hz], 2.62 [m, 1H, $CH(CH_3)_2$, J = 6.5 Hz], 2.72 [d, 1H, H(6)$_{eq}$, J = 10.6 Hz], 3.04–3.07 [m, 2H, H(2)$_{ax}$ and H(4)$_{eq}$], 3.30 [d, 1H, H(8)$_{ax}$, J = 13.2 Hz], 3.74 [d, 1H, H(8)$_{eq}$, J = 12.8 Hz], 4.77 [d, 1H, H(2)$_{eq}$, J = 13.9 Hz], 7.28–7.41 (m, 5H, Ar—H); $^{13}$C NMR (DCCl$_3$) ppm 16.30 ($CH_3$), 19.33 ($CH_3$), 29.06 [C(1)], 29.76 [C(5)], 32.29 [C(9)], 46.55 [C(2)], 52.19 [C(4)], 52.62 [C(8)], 54.34 [$CH(CH_3)_2$], 54.75 [C(6)], 126.75, 128.24, 128.67, 137.75 (Ar—C), 170.09 (C=O).

EXAMPLE XI

3-Benzoyl-7-isopropyl-3,7-diazabicyclo[3.3.1]nonane Hydroperchlorate (1)

A 250-mL Erlenmeyer flask was equipped with a magnetic stirrer and an ice bath. To a chilled (5° C.), stirred solution of the amide (32, 1.52 g, 5.58 mmol) in ether (60 mL) was added dropwise $HClO_4$ (60%, 1.17 g, 6.98 mmol) over 10 min. Filtration gave salt (1) as a white solid which was washed with dry ether (50 mL), stirred in hot $CH_3OH$ (30 mL), cooled to −10° C. overnight, filtered, and dried (vacuum pump, 61° C./0.2 mm Hg, overnight) to afford 1.90 g (91.3%) of pure salt (1); mp 226°-227° C. (dec): IR (KBr) cm$^{-1}$ 3150 (N—H), 2990, 2960, 2935, 2920, 2885 (C—H), 1635 (C=O), 1100 (Cl—O), 740, 710 (C—H out of plane, mono); $^1$H NMR [(D$_3$C)$_2$C=O] δ1.55 (d, 6H, $CH_3$, J = 6.6 Hz), 1.97 [bd, 1H, H(9), J = 13.0 Hz], 2.18 [bd, 1H, H(9), J = 13.2 Hz], 2.51 [bs, 2H, H(1,5)], 3.30 [bd, 2H, H(2,4)$_{ax}$, J = 13.2 Hz], 3.65 [m, 2H, H(6,8)$_{ax}$], 3.83 [h, 1H, —$CH(CH_3)_2$, J = 6.8 Hz], 3.94 [bd, 2H, H(2,4)$_{eq}$, J = 12.3 Hz], 4.23 [bd, 2H, H(6,8)$_{eq}$, J = 13.2 Hz], 7.45–7.50 (m, 5H, Ar—H), 7.85 (bs, 1H, N—H); $^{13}$C NMR (DMSO-d$_6$, 80° C.) ppm 16.34 ($CH_3$), 26.69 [C(1,5)], 27.62 [C(9)], 48.80 [C(2,4)], 52.31 [C(6,8)], 59.91 [$CH(CH_3)_2$], 127.05, 128.30, 129.40, 136.40 (Ar—C), 172.86 (C=O). Anal. Calcd. for $C_{17}H_{25}ClN_2O_5$: C, 54.76; H, 6.76. Found: C, 54.43; H, 6.78.

EXAMPLE XII

3-(3',4'-Dimethoxybenzyl)-7-isopropyl-3,7-diazabicyclo[3.3.1]nonan-9-one (23)

A 200-mL, three-necked, round-bottomed flask was equipped with a magnetic stirrer, a heating mantle, a standard condenser with a N$_2$ inlet, a 50-mL addition funnel, and a glass stopper. A mixture containing 3,4-dimethoxybenzylamine (8.36 g, 50 mmol), paraformaldehyde (3.15 g, 105 mmol) and $CH_3OH$ (35 mL) was made acidic with the addition of glacial acetic acid (3.0 g, 50 mmol). Stirring the mixture under N$_2$ for 20 min was followed by the dropwise addition of 1-isopropyl-4-piperidinone (42, 7.06 g, 50 mmol) and glacial acetic acid (3.0 g, 50 mmol) in CH$_3$OH (25 mL) over 1.25 h. Boiling of the mixture was continuous for an additional 23 h. This new mixture was evaporated to give a red viscous oil. After dissolving the oil in H$_2$O (100 mL), the solution was extracted (ether, 2×100 mL), the latter being discarded. Chilling (ice water bath) of the water layer below 10° C., followed by basification (pH ~12) with KOH pellets (6.6 g, 100 mmol), produced an orange suspension which was extracted (CH$_2$Cl$_2$, 4×80 mL). Combined extracts were dried (Na$_2$SO$_4$, overnight), filtered, and concentrated to give a crude oil. This oil was digested in 250 mL of Skelly B (bp 60°-68° C.) for 0.5 h and the supernatant was decanted. Evaporation of the solvent gave an oil which, when distilled (175°-205° C./10$^{-4}$ mm Hg), afforded a yellow oil. Adding Skelly B induced crystallization to give 4.32 g (26%) of off white ketone (23); mp 79.5°-80.5° C. IR (KBr) cm$^{-1}$ 3095, 3015 (Ar—H), 2980, 2955, 2920, 2855, 2810 (C—H), 1745 (C=O), 1620, 1605 (C=C); $^1$H NMR (DCCl$_3$) δ1.03 (d, 6H, CH$_3$, J=6.6 Hz), 2.59 [bs, 2H, H(1,5)], 2.81-2.90 [m, 5H, ring protons and CH(CH$_3$)$_2$], 2.98 (dd, 2H, ring protons, J=10.7 Hz, J'=3.2 Hz), 3.08 (dd, 2H, ring protons, J=10.7 Hz, J'=2.99 Hz), 3.47 (s, 2H, ArCH$_2$), 3.87 (s, 3H, OCH$_3$), 3.88 (s, 3H, OCH$_3$), 6.80-6.92 (m, 3H, Ar—H); $^{13}$C NMR (DCCl$_3$) ppm 18.17 (CH$_3$), 46.85 [C(1,5)], 53.40 [CH(CH$_3$)$_2$], 53.86 [C(2,4)], 55.76, 55.86 (OCH$_3$), 58.01 [C(6,8)], 60.93 (ArCH$_2$), 110.60, 111.46, 120.68, 131.30, 148.04, 148.90 (Ar—C), 215.27 (C=O); $^{15}$N NMR (DCCl$_3$) ppm 39.66 [N(7)], 40.93 [N(3)]. Anal. Calcd. for C$_{19}$H$_{28}$N$_2$O$_3$: C, 68.65; H, 8.49. Found: C, 68.70; H, 8.53.

EXAMPLE XIII 7-(3',4'-Dimethoxybenzyl)-3-isopropyl-3,7-diazabicyclo[3.3.1]nonane Hydroperchlorate (7)

To a mixture of KOH pellets (85%, 2.38 g, 36 mmol) and the ketone (23, 1.0 g, 3 mmol) in triethylene glycol (25 mL) was added hydrazine (95%, 1.01 g, 30 mmol) in one portion in a 70-mL, jacketed flask equipped with a magnetic stirrer, a heating mantle, a standard condenser, a lower take-off condenser and two glass stoppers. A heating temperature of 150°-160° C. for 3.5 h was achieved by using tetralin (bp 207° C.) in the jacket. After cooling to RT, the solution was diluted with cold H$_2$O (50 mL) and extracted with ether (3×40 mL). Combined extracts were washed with 10% NaOH (50 mL) and saturated NaCl (50 mL), dried (Na$_2$SO$_4$, overnight), filtered, and concentrated to afford a yellow oil (0.78 g). Dissolution of the oil in ether (50 mL) with magnetic stirring and cooling (5° C., via ice water bath) in a 125-mL Erlenmeyer flask (equipped with an external ice bath) was followed by the dropwise addition of a solution of HClO$_4$ (60%, 0.51 g, 3.06 mmol) over 10 min. Filtering the precipitate, washing the latter with ether (~50 mL), and then recrystallizing (95% EtOH) gave 0.79 g (62.9%) of white salt (3); mp 127.5°-128.0° C. (dec). IR (KBr) cm$^{-1}$ 3020 (Ar C—H), 2955, 2930, 2840, 2815, 2790 (C—H), 1610 (C=C), 1090 (Cl—O); $^1$H NMR (DMSO-d$_6$) δ1.15 (d, 6H, CH$_3$, J=6.7 Hz), 1.64 [d, 1H, H(9), J=12.1 Hz], 1.80 [d, 1H, H(9), J=13.0 Hz], 2.14 [bs, 2H, H(1,5)], 2.50 [d, 2H, H(6,8)$_{ax}$, J=10.4 Hz], 3.05-3.14 [m, 4H, H(6,8)$_{eq}$ and H(2,4)$_{ax}$], 3.28 [d, 2H, H(2,4)$_{eq}$, J=11.6 Hz], 3.39 [m, 1H, CH(CH$_3$), J=6.7 Hz], 3.49 (s, 2H, ArCH$_2$), 3.75, 3.76 (two s, 6H, OCH$_3$), 6.86-7.08 (m, 3H, Ar—H); $^{13}$C NMR (DMSO-d$_6$) ppm 16.25 (CH$_3$), 27.23 [C(1,5)], 29.79 [C(9)], 52.74 [C(2,4)], 55.31, 55.36 (OCH$_3$), 55.78 [CH(CH$_3$)$_2$], 56.85 [C(6,8)], 60.89 (ArCH$_2$), 111.23, 113.01, 122.02, 128.00, 148.38, 148.66 (Ar—C); $^{15}$N NMR (DMSO-d$_6$) ppm 52.22 [N(7)], 59.43 [N(3)]. Anal. Calcd. for C$_{19}$H$_{31}$ClN$_2$O$_6$: C, 54.48; H, 7.46. Found: C, 54.76; H, 7.61.

EXAMPLE XIV 7-(4'-Chlorobenzyl)-3-isopropyl-3,7-diazabicyclo[3.3.1]nonan-9-one (22)

A 200-mL, three-necked, round-bottomed flask was equipped with a magnetic stirrer, a heating mantle, a standard condenser with a N$_2$ inlet, a 50-mL, an addition funnel and a glass stopper. A mixture of 4-chlorobenzylamine (7.08 g, 50 mmol), paraformaldehyde (3.15 g, 105 mmol), glacial acetic acid (3.0 g, 50 mmol), and CH$_3$OH (35 mL) was brought to gentle reflux with stirring under N$_2$ for 15 min. To the mixture was added dropwise a solution of 1-isopropyl-4-piperidinone (42, 7.06 g, 50 mmol) and glacial acetic acid (3.0 g, 50 mmol) in CH$_3$OH (25 mL) over 1 h. Boiling of the mixture was continued for an additional 24 h. After concentrating to a viscous red oil, the reaction mixture was then diluted with H$_2$O (100 mL) and extracted (ether, 3×100 mL), the latter being discarded. Chilling (via ice water bath) of the aqueous layer to below 10° C. was followed by basification (pH ~13) with KOH pellets (85%, 6.6 g, 100 mmol). Combined extracts (ether, 3×60 mL) were dried (Na$_2$SO$_4$, 4 h), filtered, and concentrated to give a viscous red oil. This oil was digested in pentane (100 mL) for 20 min and the supernatant was decanted and concentrated Distillation of the resulting oil (195°-205° C./10$^{-5}$ mm Hg) gave 5.25 g of a yellow oil which solidified upon standing. Recrystallization (pentane) of the solid gave 3.46 g (22.6%) of white crystalline (22); mp 68°-69° C. IR (KBr) cm$^{-1}$ 3030 (Ar C—H), 2955, 2880, 2800 (C—H), 1730 (C=O), 800 (C—H out of plane, para); $^1$H NMR (DCCl$_3$) δ1.03 (d, 6H, CH$_3$, J=6.3 Hz), 2.58 [bs, 2H, H(1,5)], 2.80-3.05 [m, 9H, ring protons and CH(CH$_3$)$_2$], 7.27 (s, 4H, Ar—H); $^{13}$C NMR (DCCl$_3$) ppm 18.25 (CH$_3$), 46.85 [C(1,5)], 53.40 [CH(CH$_3$)$_2$], 53.76 [C(2,4)], 57.92 [C(6,8)], 60.48 (ArCH$_2$), 128.40, 129.95, 132.74, 137.21 (Ar—C), 215.04 (C=O); $^{15}$N NMR (DCCl$_3$) ppm 39.18 [N(3)], 40.31 [N(7)]. Anal. Calcd. for C$_{17}$H$_{23}$ClN$_2$O: C, 66.55; H, 7.56. Found: 66.47; H, 7.52.

EXAMPLE XV 7-(4'-Chlorobenzyl)-3-isopropyl-3,7-diazabicyclo[3.3.1]nonane Hydroperchlorate (6)

To a mixture of KOH pellets (85%, 1.72 g, 26.1 mmol) and the ketone (22, 1.0 g, 3.26 mmol) in triethylene glycol (30 mL) was added hydrazine (95%, 0.44 g, 13.0 mmol) in one portion in a 150-mL, jacketed flask equipped with a magnetic stirrer, a heating mantle, a standard condenser, a lower take-off condenser with a N$_2$ inlet, and three glass stoppers. A heating temperature of 200°-210° C. for 4 h under N$_2$ was produced by boiling tetralin (bp 207° C.) in the jacket. Cooling of the solution to RT was followed by the addition of chilled water (40 mL). Combined extracts of the resulting suspension (ether, 4×30 mL) were washed with 10% NaOH (30 mL) and saturated NaCl (30 mL), dried (Na$_2$SO$_4$, 4 h), filtered and concentrated to a light yellow oil which displayed no carbonyl stretch in the IR spectrum and was used without further purification. Dissolution of the oil in ether (60 mL) at −5° C. (via ice water bath) was followed by the dropwise addition of a solution of HClO$_4$ (60%, 0.68 g, 4.08 mmol) in (H$_3$C)$_2$CHOH (1 mL) over 5 min. The resulting, precipitated solid was filtered and recrystallized (95% EtOH) to give 0.81 g (63.3%) of white crystals of (6); mp 140°-141° C. IR (KBr) cm$^{-1}$ 3060, 3020 (Ar C—H), 2970, 2920, 2830 (C—H), 1485 (C=C), 1085 (Cl—O), 790 (C—H out of plane, para); $^1$H NMR (DMSO-d$_6$) δ1.19 (d, 6H, CH$_3$, J=6.7 Hz), 1.61 [d, 1H, H(9), J=12.7 Hz], 1.82 [d, 1H, H(9), J=12.2 Hz], 2.14 [bs, 2H, H(1,5)], 2.41 [bd, 2H, H(6,8)$_{ax}$, J=11.2 Hz], 3.04 [bd, 2H, H(6,8)$_{eq}$, J=11.1 Hz], 3.16 [bd, 2H, H(2,4)$_{ax}$, J=11.2 Hz], 3.34 [bd, 2H, H(2,4)$_{eq}$, J=11.7 Hz], 3.44-3.52 [m, 3H, CH(CH$_3$)$_2$ and ArCH$_2$], 7.44 [s, 4H, Ar—H]; $^{13}$C NMR (DMSO-d$_6$) ppm 16.10 (CH$_3$), 27.25 [C(1,5)], 29.60 [C(9)], 52.77 [C(2,4)], 56.25 [CH(CH$_3$)$_2$], 56.75 [C(6,8)], 60.42 (ArCH$_2$), 128.28, 131.27, 132.14, 135.72 (Ar—C); $^{15}$N NMR (DMSO-d$_6$) ppm 50.34 [N(7)], 60.57 [N(3)]. Anal. Calcd. for C$_{17}$H$_{20}$Cl$_2$N$_2$O$_4$: C, 51.92; H, 6.66. Found: C, 51.74; H, 6.57.

EXAMPLE XVI 3-(4'-Chlorobenzoyl)-7-isopropyl-3,7-diazabicyclo[3.3.1]nonane (33)

A 25-mL, three-necked, round-bottomed flask was equipped with a magnetic stirrer, a standard condenser with a N$_2$ inlet, a 10-mL addition funnel and two glass stoppers. To a mixture of the amine (31, 0.60 g, 3.57 mmol) in CH$_2$Cl$_2$ (5 mL) and 10% NaOH (3.58 g, 8.93 mmol) was added dropwise a solution of 4-chlorobenzoyl chloride (0.69 g, 3.92 mmol) in CH$_2$Cl$_2$ (5 mL) over 15 min. Stirring of the mixture was continued for an additional 3 h under N$_2$. An aqueous mixture, formed upon addition of H$_2$O (30 mL), was extracted (CH$_2$Cl$_2$, 4×25 mL). Combined extracts were dried (Na$_2$SO$_4$, 2 h), filtered, and concentrated to give a viscous yellow oil. Chromatography of the oil was performed by adding an ether solution of the oil to a neutral alumina column (69 g, 1.7 cm×30 cm) and then using 60:40 hexanes/ethyl acetate as eluant. Fractions (R$_f$=0.41) were saved and concentrated (rotary evaporator then vacuum pump, overnight, RT/0.2 mm Hg) to give 0.86 g (80.4%) of off-white solid (33); mp 97°-98° C. IR (KBr) cm$^{-1}$ 3085, 3070 (Ar C—H), 2965, 2935, 2865, 2800, 2770 (C—H), 1630 (C=O); $^1$H NMR (DCCl$_3$) δ0.95 (d;, 3H, CH$_3$, J=6.5 Hz), 1.05 (d, 3H, CH$_3$, J=6.4 Hz), 1.63-1.75 [m, 3H, H(5) and H(9)], 1.97 [bs, 1H, H(1)], 2.41 [bd, 1H, H(4)$_{ax}$, J=10.6 Hz], 2.50 [bd, 1H, H(6)$_{ax}$, J=11.2H], 2.59 [heptet, 1H, CH(CH$_3$)$_2$, J=6.5 Hz], 2.71 [bd, 1H, H(6)$_{eq}$, J=11.0 Hz], 3.03-3.06 [m, 2H, H(2)$_{ax}$ and H(4)$_{eq}$], 3.31 [bd, 1H, H(8)$_{ax}$, J=12.8 Hz], 3.71 [bd, 1H, H(8)$_{eq}$, 13.1 Hz], 4.77 [bd, 1H, H(2)$_{eq}$, J=13.2 Hz], 7.27-7.37 (m, 4H, Ar—H); $^{13}$C NMR (DCCl$_3$) ppm 16.37, 19.35 (CH$_3$), 29.07 [C(1)], 29.07 [C(1)], 29.80 [C(5)], 32.29 [C(9)], 46.68 [C(2)], 52.22 [C(4)], 52.56 [C(8)], 54.38 [CH(CH$_3$)$_2$], 54.79 [C(6)], 128.35, 128.51, 134.67, 136.11 (Ar—C), 169.03 (C=O). Anal. Calcd. for C$_{17}$H$_{23}$ClN$_2$O: C, 66.55; H, 7.56. Found: C, 66.45; H, 7.71.

EXAMPLE XVII

β,β'-Dibromoisobutyric Acid (46)

Into a 500-mL, single necked, round-bottomed flask equipped with a heating mantle, a magnetic stirrer, a Claisen distillation head, a standard condenser and a receiver were placed diethyl bis(hydroxymethyl)malonate (45, 37 g, 0.17 mol), and hydrobromic acid (48%, 280 mL, 2.5 mol). The resulting homogeneous solution was distilled for 2.5 h (35°-126° C.), and 100 mL of distillate was collected. Heating was momentarily stopped, and the distillation head, condenser and receiver were removed and replaced with a condenser. The mixture was heated at reflux for 6 h. A brown reaction mixture was poured into a 250 mL Erlenmeyer flask which was allowed to cool to RT (1 h) and then was placed in an ice bath (1 h) to yield acid (46) as a white solid. This white solid was filtered off using a Buchner funnel under suction (aspirator) and was then washed with cold H$_2$O (50 mL) to afford, after drying (Abderhalden, 78° C., 12 h/0.2 mm Hg, P$_2$O$_5$), acid (19.1 g, 46.3%); mp 96°-97° C. The mother liquor was concentrated to about 75 mL and then cooled to RT (0.5 h) [followed by an ice bath (0.5 h)] to yield a second crop of the acid (46) (3.7 g, 9.0%); mp 95°-97° C. IR (KBr) cm$^{-1}$ 3500-2500 (CO$_2$H), 1700 (C=O); $^1$H NMR (DCCl$_3$) δ3.27 (m, 1H, CH), 3.79 (m, 4H, CH$_2$Br), 10.91 (bs, 1H, CO$_2$H); $^{13}$C NMR (DCCl$_3$) ppm 29.80 (t, CH$_2$Br), 48.38 (d, CH), 175.30 (s, CO$_2$H).

EXAMPLE XVIII

Ethyl β,β'-Dibromoisobutyrate (47)

Into a 250-mL, single necked, round-bottomed flask equipped with a soxhlet extractor, standard condenser, magnetic stirrer and heating mantle were placed the dibromo acid (46, 27 g, 0.11 mol), benzene (125 mL), absolute ethanol (50 mL) and conc H$_2$SO$_4$ (0.5 mL). Into the Soxhlet extractor was placed a thimble containing anhydrous MgSO$_4$ (20 g). The reaction mixture was heated at reflux for 24 h. Solvent was distilled off until about 50 mL remained. The concentrated reaction mixture was cooled to RT (0.5 h), and H$_2$O (50 mL) was added followed by slow addition of solid NaHCO$_3$ with stirring until the pH was 7. The resulting suspension was transferred to a separatory funnel and the organic layer was separated. The aqueous layer was extracted with ether (3×50 mL). The organic layers were combined and washed with H$_2$O (50 mL) and saturated NaCl (50 mL). This was followed by drying (anhydrous MgSO$_4$, 2 h), filtration, and evaporation (rotary evaporator, aspirator) to yield a pale brown liquid which was distilled under reduced pressure to yield the ester (47,.3 g, 94.9%), bp 60°-62° C./0.2 mm Hg. IR (film) cm$^{-1}$ 1735 (C=O); $^1$H NMR (DCCl$_3$) δ1.30 (t, 3H, CH$_3$), 3.20 (m, 1H, CH), 3.78 (m, 4H, CH$_2$Br), 4.25 (q, 2H, OCH$_2$); $^{13}$C NMR (DCCl$_3$) ppm 14.18 (q, CH$_3$), 30.75 (t, CH$_2$Br), 48.52 (d, CH), 61.66 (t, OCH$_2$), 169.32 (s, CO$_2$Et).

EXAMPLE XIX

Ethyl 3-Benzyl-3-azabicyclo[3.3.1]nonan-9-one-7-(endo)-carboxylate (20)

As the starting point for the preparation of (20), the preparation of 1-benzyl-4-pyrrolidinyl-1,2,3,6-tetrahydropyridine was required. Into a 250-mL, single-necked, round-bottomed flask equipped with a Dean-Stark trap, standard condenser, magnetic stirrer, heating mantle, and a N$_2$ inlet were placed 1-benzyl-4-piperidinone (43, 10.2 g, 55 mmol), benzene (125 mL) and pyrrolidine (6.0 g, 85 mmol). The resulting mixture was heated at reflux for 24 h. The Dean-Stark trap was removed and a simple distillation apparatus was installed. Distillation of the solvent was completed at atmospheric pressure followed by another distillation under reduced pressure to yield the enamine as a pale yellow oil (12.7 g, 97.0%), bp 167°-169° C./0.2 mm Hg. IR (film) cm$^{-1}$ 1650 (C=C—N); $^1$H NMR (DCCl$_3$) δ1.79 [bs, 4H, H(9,10)], 2.30 [bs, 2H, H(3)], 2.56 [t, 2H, H(2)], 3.00 [bs, 2H, H(8,11)], 3.05 [bs, 2H, H(6)], 3.54 (s, 2H, CH$_2$Ph), 4.16 [bs, 1H, H(5)], 7.26-7.33 (m, 5H, Ar—H); $^{13}$C NMR (DCCl$_3$) ppm 24.69 [t, C(9,10)], 28.31 [t, C(3)], 47.10 [t, C(8,11)], 50.07 [t, C(2)], 52.94 [t, C(6)], 62.68 (t, CH$_2$Ph), 90.24 [d, C(5)], 126.64, 127.88, 128.92, 138.61 (Ar—C), 141.29 [s, C(4)].

Into a 250-mL, three-necked, round-bottomed flask equipped with a heating mantle, magnetic stirrer, standard condenser, dropping funnel and a N$_2$ inlet were placed a solution of the above enamine [9.9 g, 40 mmol in CH$_3$CN (50 mL)] and triethylamine (11.6 g, 9.1 g, 90 mmol). The resulting mixture was heated at reflux, and, to the boiling solution was added dropwise a solution of the dibromo ester (47, 11.1 g, 40 mmol) in CH$_3$CN (20 mL) over a period of 0.5 h. During addition, triethylammonium bromide precipitated as a white solid, and the reaction mixture turned brown. Heating was continued for 3.5 h after the addition was complete. Solvent was removed (rotary evaporator) to yield a dark brown oil to which was added H$_2$O (50 mL). The mixture was extracted with HCCl$_3$ (4×50 mL). The organic layers were combined and washed successively with HCl (1N, 2×50 mL), NaHCO$_3$ (saturated aqueous, 2×50 mL) and NaCl (saturated, 2×50 mL). After drying (anhydrous Na$_2$SO$_4$), the solution was filtered and evaporated (rotary evaporator) to yield the crude ketone (20) as a dark brown oil. This dark brown oil was purified by column chromotography over silica gel (150 g, 3.8 cm×61 cm; 1 mL/min) using 10% EtOAc in hexanes as the eluant to yield ketone (20) as a pale yellow, viscous oil (4.1 g, 33.0%). R$_f$=0.49 in 9:1 hexanes:EtOAc. IR (film) cm$^{-1}$ 1730 (C=O); $^1$H NMR (DCCl$_3$) δ1.30 (t, 3H, CH$_3$), 2.18 [dd, 2H, H(6,8)$_{ax}$, J=6.9, 15.9 Hz], 2.29 [bs, 2H, H(1,5)], 2.44 [m, 3H, H(6,8)$_{eq}$ and H(7)$_{exo}$], 2.82 [dd, 2H, H(2,4)$_{ax}$, J=6.0, 14.4 Hz], 3.04 [d, 2H, H(2,4)$_{eq}$, J=10.6 Hz], 3.56 (s, 2H, CH$_2$Ph), 4.22 (q, 2H, OCH$_2$), 7.17-7.30 (m, 5H, Ar—H); $^{13}$C NMR (DCCl$_3$) ppm 14.35 (q, CH$_3$), 33.21 [t, C(6,8)], 37.75 [d, C(7)], 46.61 [d, C(1,5)], 58.06 (t, CH$_2$Ph), 60.34 (t, OCH$_2$), 127.26, 128.09, 129.50, 135.10 (Ar—C), 172.40 (s, CO$_2$Et), 215.92 (C=O). The oil, very slightly crude (20), was used without further purification for succeeding steps since the oil decomposed upon attempted distillation.

EXAMPLE XX

Ethyl 3-Benzyl-9,9-(1,3-dithiolan-2-yl)-3-azabicyclo[3.3.1]nonane-7-(endo)-carboxylate (38)

Into a 100-mL, three-necked, round-bottomed flask equipped with a magnetic stirrer, standard condenser, dropping funnel, N$_2$ inlet and an ice-bath were placed the ketone (20, 3.01 g, 10 mmol), 1,2-ethanedithiol (2 mL, 2.25 g, 24 mmol), and dry HCCl$_3$ (50 mL). The resulting mixture was cooled to 0°-5° C. in an ice bath. Freshly distilled BF$_3$ etherate (4 mL, 2.2 g, 15 mmol) was added dropwise over a period of 0.5 h. The reaction mixture was stirred at 0°-5° C. for 1 h and then at RT for 8 h. To the resulting mixture was added HCCl$_3$ (25 mL), and the solution was successively washed with NaOH (1N, 3×50 mL) and NaCl (saturated, 50 mL). After drying (anhydrous Na$_2$SO$_4$), the solution was filtered and evaporated (rotary evaporator, aspirator) to yield the crude thioketal (38) as a pale yellow, viscous oil, which was purified by column chromatography over silica gel (105 g) using 10% EtOAc in hexanes as the eluant. The thioketal was obtained as a colorless oil which crystallized out as a white solid upon standing at RT (12 h). This white solid was recrystallized (hexanes) to yield solid thioketal (38) as white needles (1.6 g, 42.0%, mp 76°-78° C.). IR (KBr) cm$^{-1}$ 1715 (CO$_2$Et); $^1$H NMR (DCCl$_3$) δ1.30 (t, 3H, CH$_3$), 1.90 [bs, 2H, H(1,5)], 2.34 [bd, 2H, H(6,8)$_{ax}$], 2.47 [m, 1H, H(7)], 2.68-2.83 [m, 6H, H(6,8)$_{eq}$, H(2,4)$_{ax}$ and H(2,4)$_{eq}$], 3.10-3.17 (m, 4H, SCH$_2$), 3.44 (s, 2H, CH$_2$Ph), 4.19 (q, 2H, OCH$_2$), 7.12-7.33 (m, 5H, Ar—H); $^{13}$C NMR (DCCl$_3$) ppm 14.36 (q, CH$_3$), 30.25 [t, C(6,8)], 36.71 [d, C(7)], 38.21, 38.64 (t, SCH$_2$), 42.10 [d, C(1,5)], 54.92 [t, C(2,4)], 60.14 (t, CH$_2$Ph), 60.27 (t, OCH$_2$), 127.00, 127.84, 129.91, 134.21 (Ar—C), 172.35 (CO$_2$Et). Anal. Calcd. for C$_{20}$H$_{27}$NO$_2$S$_2$: C, 63.66; H, 7.16; S, 16.97. Found: C, 63.99; H, 7.08; S, 17.23.

EXAMPLE XXI

Ethyl 3-Benzyl-9,9-(1,3-dithiolan-2-yl)-3-azabicyclo[3.3.1]nonane-7-(endo)-carboxylate Hydroperchlorate (14)

Into a 250-mL Erlenmeyer flask equipped with a magnetic stirrer were placed the thioketal (38, 1.5 g, 4 mmol), anhydrous ether (150 mL), and absolute ethanol (5 mL). The resulting solution was cooled in an ice bath for 0.5 h. To this cooled solution was added dropwise HClO$_4$ (60%, 0.85 g, 5 mmol) over a period of 0.5 h. During the addition a white solid precipitated. The resulting mixture was stirred in an ice bath for another 1 h, after the addition was complete, and then for 2 h at RT. The white solid obtained by filtration was recrystallized (isopropyl alcohol) to yield the thioketal hydroperchlorate (14) as white needles (1.7 g, 90.0%); mp 153°-154° C. IR (KBr) cm$^{-1}$ 3400 (N—H), 1700 (CO$_2$Et), 1100 (Cl—O); $^1$H NMR (DCCl$_3$) δ1.30 (t, 3H, CH$_3$), 2.05 [d, 2H, H(6,8)$_{ax}$, J=16.1 Hz], 2.36 [bs, 2H, H(1,5)], 2.71 [m, 2H, H(6,8)$_{eq}$], 3.33 (m, 4H, SCH$_2$), 3.50 [m, 2H, H(2,4)$_{ax}$], 3.68 (d, 2H, CH$_2$Ph), 7.43-7.60 (m, 5H, Ar—H), 10.30 (bs, 1H, N—H); $^{13}$C NMR (DCCl$_3$) ppm 13.79 (q, CH$_3$), 28.42 [t, C(6,8)], 29.53 [d, C(7)], 39.18 [d, C(1,5)], 39.51, 39.88 (t, SCH$_2$), 56.60 [t, C(2,4)], 61.81 (t, CH$_2$Ph), 63.67 (t, OCH$_2$), 68.96 [s, C(9)], 127.84, 129.93, 130.31, 131.57 (Ar—C), 183.05 (s, CO$_2$Et). Anal. Calcd. for C$_{20}$H$_{28}$ClNO$_6$S$_2$: C, 50.26; H, 5.86; N, 2.93. Found: C, 50.24; H, 6.12; N, 2.94.

EXAMPLE XXII

Ethyl 3-Benzyl-3-azabicyclo[3.3.1]nonane-7-(endo)-carboxylate Hydroperchlorate (13)

Ester (38) (1.89 g, 0.005 mol), ethanol (200 mL), and Raney nickel (about 20 mL of a wet solid) were heated together at reflux for 18 hours, and the mixture was allowed to cool. After the mixture was filtered, the solvent was evaporated to a viscous oil. The oil was treated with a saturated brine solution, and the resulting mixture was extracted with chloroform (3×50 mL). Evaporation of the solvent gave a colorless oil (0.97 g, 68.0%). Thus, slightly crude ethyl 3-benzyl-3-azabicyclo[3.3.1]nonane-7-(endo)-carboxylate was used in the next step without further purification.

Into a 250 mL Erlenmeyer flask equipped with magnetic stirrer were placed the above ester (0.95 g, 3 mmol), anhydrous ether (150 mL), and absolute ethanol (5 mL). The resulting solution was cooled in ice bath and to the chilled solution was added dropwise $HClO_4$ (60%, 0.75 g, 4.5 mmol) over a period of 0.5 h. During the addition, a white solid precipitated. The resulting mixture was stirred in ice bath for 1 h, after the addition was complete, and then for 2 h at RT. Filtration and recrystallization (isopropyl alcohol) yielded the hydroperchlorate (13) as colorless platelets (0.87 g, 68.0%); mp 130°-131° C. IR (KBr) cm$^{-1}$ 3440 (N—H), 1700 ($CO_2Et$), 1100 (Cl—O); $^1$H NMR ($DCCl_3$) δ1.30 (t, 3H, $CH_3$), 1.61 [bd, 1H, H(9)$_{endo}$], 1.87 [d, 2H, H(6,8)$_{ax}$, J=12 Hz], 2.05 [bd, 1H, H(9)$_{exo}$], 2.16-2.31 [m, 4H, H(1,5) and H(6,8)$_{eq}$], 2.91-2.98 [m, 1H, H(7)], 3.35-3.48 [m, 4H, H(2,4)$_{ax}$ and H(2,4)$_{eq}$], 4.32 (q, 2H, $OCH_2$), 4.50 (d, 2H, $CH_2Ph$), 7.38-7.68 (m, 5H, Ar—H); $^{13}$C NMR ($DCCl_3$) ppm 13.79 (q, $CH_3$), 25.74 [d, C(1,5)], 27.85 [t, C(6,8)], 31.91 [d, C(7)], 55.96 [t, C(2,4)], 61.68 (t, $CH_2Ph$), 63.05 (t, $OCH_2$), 128.60, 129.98, 131.25, (Ar—C), 182.93 (s, $CO_2Et$). Anal. Calcd. for $C_{18}H_{26}ClNO_6$: C, 55.75; H, 6.71. Found: C, 56.11; H, 6.82.

EXAMPLE XXIII

7-Isopropyl-3-(3',4',5'-trimethoxybenzoyl)-3,7-diazabicyclo[3.3.1]nonane (35)

A 25-mL, three-necked, round-bottomed flask was equipped with a magnetic stirrer, a standard condenser with $N_2$ inlet, a 10-mL addition funnel and two glass stoppers. To a mixture of the amine (31, 0.60 g, 3.57 mmol) in $CH_2Cl_2$ (5 mL) and 10% NaOH (3.58 g, 8.93 mmol) was added dropwise a solution of 3,4,5-trimethoxybenzoyl chloride (0.92 g, 3.92 mmol) in $CH_2Cl_2$ (5 mL) over 15 min. Stirring of the mixture was continued for an additional 3 h under $N_2$. An aqueous mixture, upon addition of $H_2O$ (30 mL), was extracted ($CH_2Cl_2$, 4×25 mL). Combined extracts were dried ($Na_2SO_4$, 2 h), filtered, and concentrated to give a viscous yellow oil. Chromatography of the oil was performed on neutral alumina (74 g, 1.7 cm×32 cm) using 60:40 ethyl acetate/hexanes as eluant. Fractions ($R_f$=0.34) were saved and concentrated (rotary evaporator then vacuum pump, overnight, RT/0.2 mm Hg) to give 1.02 g (79.1%) of off-white solid (35); mp 67.5°-69.5° C. IR (KBr) cm$^{-1}$ 3055 (Ar C—H), 2985, 2955, 2910, 2890, 2780 (C—H), 1620 (C=O); $^1$H NMR ($DCCl_3$) δ0.96 (d, 3H, $CH_3$, J=6.5 Hz), 1.09 (d, 3H, $CH_3$, J=6.7 Hz), 1.64-1.79 [m, 3H, H(5) and H(9)], 2.05 [bs, 1H, H(1)], 2.44 [bd, 1H, H(4)$_{ax}$, J=10.6 Hz], 2.57 [bd, 1H, H(6)$_{ax}$, J=10.8 Hz], 2.66 [heptet, 1H, $CH(CH_3)_2$, J=6.6 Hz], 2.71 [bd, 1H, H(6)$_{eq}$, J=11.0 Hz], 3.02-3.07 [m, 2H, H(4)$_{eq}$ and H(2)$_{ax}$], 3.31 [bd, 1H, H(8)$_{ax}$, J=13.2 Hz], 3.80-3.92 [m, 10H, H(8)$_{eq}$ and $OCH_3$], 4.77 [bd, 1H, H(2)$_{eq}$, J=13.5 Hz], 7.29 (s, 2H, Ar—H); $^{13}$C NMR ($DCCl_3$) ppm 15.87, 19.42 ($CH_3$), 29.02 [C(1)], 29.78 [C(5)], 32.35 [C(9)], 46.64 [C(2)], 51.73 [C(4)], 52.48 [C(8)], 54.39 [$CH(CH_3)_2$], 54.95 [C(6)], 56.13, 60.86 ($OCH_3$), 103.83, 133.32, 133.21, 138.22, 153.21 (Ar—C), 169.66 (C=O). Anal. Calcd. for $C_{20}H_{30}N_2O_4$: C, 66.27; H, 8.34. Found: C, 66.04; H, 8.32.

EXAMPLE XXIV 3-(3',4'-Dimethoxybenzoyl)-7-isopropyl-3,7-diazabicyclo[3.3.1]nonane (34)

A 25-mL, three-necked, round-bottomed flask was equipped with a magnetic stirrer, a standard condenser with a $N_2$ inlet, a 10-mL addition funnel, and two glass stoppers. To a mixture of the amine (31, 0.60 g, 3.57 mmol) in $CH_2Cl_2$ (5 mL) and 10% NaOH (3.58 g, 8.93 mmol) was added dropwise a solution of 3,4-dimethoxybenzoyl chloride (0.80 g, 3.92 mmol) in $CH_2Cl_2$ (10 mL) over 15 min. Stirring of the mixture was continued for an additional 3 h under $N_2$. An aqueous mixture, formed upon addition of $H_2O$ (30 mL), was extracted ($CH_2Cl_2$, 4×25 mL). Combined extracts were dried ($Na_2SO_4$, 2 h), filtered and concentrated to give a viscous yellow oil. Chromatography of the oil was performed on neutral alumina (74 g, 1.7 cm×32 cm) using 60:40 ethyl acetate/hexanes as eluant. Fractions ($R_f$=0.31) were saved and concentrated (rotary evaporator then vacuum pump, overnight, RT/0.2 mm Hg) to give 0.87 g (73.1%) of off-white solid (34); mp 67.5°-69.5° C. IR (KBr) cm$^{-1}$ 3055 (Ar C—H), 2950, 2915, 2845, 2820, 2770, 2750, 2710 (C—H), 1625 (C=O); $^1$H NMR ($DCCl_3$) δ0.96 (d, 3H, $CH_3$, J=6.4 Hz), 1.06 (d, 3H, $CH_3$, J=6.5 Hz), 1.62-1.75 [m, 3H, H(5) and H(9)], 1.96 [bs, 1H, H(1)], 2.43 [bd, 1H, H(4)$_{ax}$, J=9.7 Hz], 2.51 [bd, 1H, H(6)$_{ax}$, J=10.5 Hz], 2.62 [heptet, 1H, $CH(CH_3)_2$, J=6.4 Hz], 2.74 [bd, 1H, H(6)$_{eq}$, J=9.9 Hz], 3.00-3.09 [m, 2H, H(4)$_{eq}$ and H(2)$_{ax}$], 3.32 [bd, 1H, H(8)$_{ax}$, J=13.2 Hz], 3.83-3.94 [m, 7H, H(8)$_{eq}$ and $OCH_3$], 4.77 [bd, 1H, H(2)$_{eq}$, J=13.3 Hz], 6.84-6.94 (m, 3H, Ar—H); $^{13}$C NMR ($DCCl_3$) ppm 16.46, 19.15 ($CH_3$), 29.13 [C(1)], 29.86 [C(5)], 32.36 [C(9)], 46.71 [C(2)], 52.25 [C(4)], 52.65 [C(8)], 54.35 [$CH(CH_3)_2$], 54.68 [C(6)], 55.88, 55.93 ($OCH_3$), 110.50, 119.64, 130.23, 148.78, 149.39 (Ar—C), 169.90 (C=O). Anal. Calcd. for $C_{19}H_{28}N_2O_3$: C, 68.65; H, 8.49. Found: C, 68.58; H, 8.47.

EXAMPLE XXV 3-(3',4'-Dimethoxybenzoyl)-7-isopropyl-3,7-diazabicyclo[3.3.1]nonane Hydroperchlorate (3)

A 50-mL Erlenmeyer flask was equipped with a magnetic stirrer and an ice bath. To a chilled (5° C.), stirred solution of the amide (34, 0.30 g, 0.90 mmol) in ether (30 mL) was added dropwise a solution of $HClO_4$ (60%, 0.18 g, 1.08 mmol) in isopropyl alcohol (1 mL) over 10 min. A white precipitate resulted which was filtered and then stirred in hot $CH_3OH$ (10 mL) for 20 min. The mixture was filtered and dried (Abderhalden, $P_2O_5$, overnight, RT/0.2 mm Hg) to give 0.27 g (69.2%) of white solid (3); mp 235°-236° C. (dec). IR (KBr) cm$^{-1}$ 3130 (N—H), 3010 (Ar C—H), 2975, 2945, 2920 (C—H), 1635 (C=O), 1095 (Cl—O); $^1$H NMR (DMSO-d$_6$, 80° C.) δ1.33 (d, 6H, $CH_3$, J=6.7 Hz), 1.74 [bd, 1H, H(9), J=12.8 Hz], 1.91 [bd, 1H, H(9), J=13.2 Hz], 2.27 [bs, 2H, H(1,5)], 3.12 [bd, 2H, H(6,8)$_{ax}$, J=13.7 Hz], 3.19-3.28 [m, 2H, H(2,4)$_{ax}$], 3.42-3.56 [m, 3H, H(6,8)$_{eq}$ and $CH(CH_3)_2$], 3.78, 3.81 (two s, 6H, $OCH_3$), 3.97 [bd, 2H, H(2,4)$_{eq}$, J=13.6 Hz], 6.94-7.03 [m, 3H, Ar—H], 7.81 (bs, 1H, N—H); $^{13}$C NMR (DMSO-d$_6$, 80° C.) ppm 16.34 ($CH_3$), 26.81 [C(1,5)], 27.80 [C(9)], 49.06 [C(2,4)], 52.40 [C(6,8)], 55.88, 55.92 ($OCH_3$), 59.97 [$CH(CH_3)_2$], 111.85, 112.10, 120.44, 128.68, 148.74, 150.26 (Ar—C), 172.97 (C=O). Anal. Calcd. for $C_{19}H_{29}ClN_2O_7$: C, 52.72; H, 6.75. Found: C, 52.35; H, 6.77.

EXAMPLE XXVI

3-Benzenesulfonyl-7-isopropyl-3,7-diazabicyclo[3.3.1]nonane (36)

A 50-mL, three-necked, round-bottomed flask was equipped with a magnetic stirrer, a standard condenser with a $N_2$ inlet, an ice bath, a 10-mL addition funnel, and a glass stopper. To a stirred, ice cold (5° C.) mixture of the amine (31, 1.03 g, 6.12 mmol) and NaOH pellets (97%, 0.76 g, 18.4 mmol) in $H_2O$ (7 mL) and $CH_2Cl_2$(5 mL) was added dropwise a solution of benzenesulfonyl chloride (2.16 g, 12.2 mmol) in $CH_2Cl_2$(5 mL) over 30 min. Stirring of the mixture was continued for an additional 17.5 h at RT. The reaction mixture was then partioned between $H_2O$ (30 mL) and $CH_2Cl_2$(30 mL) followed by basification (pH ~ 12) of the aqueous phase. Extracts ($CH_2Cl_2$,3 × 30 mL) of the remaining water layer were combined with the initial organic layer. The solution was washed with 10% NaOH (30mL) and then saturated NaCl (30 mL); it was dried ($Na_2SO_4$, overnight), filtered, and concentrated to give an orange viscous oil. Chromatography of the oil was performed on silica gel (39 g, 1.6 cm × 62 cm) using 10% $CH_3OH/CH_2Cl_2$. Fractions ($R_f$=0.44) were saved, concentrated, and reeluted on neutral alumina (90 g, 2.5 cm × 18 cm) employing ethyl acetate as eluant. Fractions ($R_f$=0.53) were saved and concentrated. A colored impurity persisted which was removed by again eluting over silica gel (21 g, 1.6 cm × 33 cm) using 5% $CH_3OH/CH_2Cl_2$ as eluant. Fractions ($R_f$=0.34) were combined and concentrated (rotary evaporator then vacuum pump, overnight, RT/0.2 mm Hg) to give 0.54 g (28.6%) of white solid (36); mp 85.5°–86.5° C. IR (KBr) $cm^{-1}$ 3060 (Ar C—H), 2960, 2910, 2890, 2865, 2820 (C—H), 1585 (C=C), 1340, 1170 (S=O), 760, 720 (C—H out of plane, mono); $^1$H NMR (DMSO-$d_6$) δ0.88 (d, 6H, $CH_3$, J=6.5 Hz), 1.40 [bs, 2H, H(9)], 1.94 [bs, 2H, H(1,5)], 2.35 [bd, 2H, H(6,8)$_{ax}$, J=10.3 Hz], 2.53 [heptet, 1H, $CH(CH_3)_2$, J=6.5 Hz], 2.69 [bd, 2H, H(6,8)$_{eq}$, J=10.3 Hz], 2.89 [dd, 2H, H(2,4)$_{ax}$, J=11.2 Hz, J'=4.5 Hz], 3.36 [d, 2H, H(2,4)$_{eq}$, J=10.9 Hz], 7.58–7.75 (m, 5H, Ar—H); $^{13}$C NMR (DMSO-$d_6$) ppm 17.57 ($CH_3$), 27.39 [C(1,5)], 28.95 [C(9)], 48.88 [C(2,4)], 52.66[C(6,8)], 53.42 [$CH(CH_3)_2$], 126.90, 129.01, 132.36, 136.79 (Ar—C). Anal. Calcd. for $C_{16}H_{24}N_2O_2S$: C, 62.31; H, 7.85. Found: C, 62.48; H, 7.69.

EXAMPLE XXVII

7-Isopropyl-3-thia-7-azabicyclo[3.3.1]nonan-9-one (26)

A three-necked, 300-mL, round-bottomed flask was equipped with a magnetic stirrer, a heating mantle, a standard condenser with a $N_2$ inlet, and two glass stoppers. A mixture containing isopropylamine (2.96 g, 50 mmol), paraformaldehyde (12.01 g, 400 mmol), and $CH_3OH$(188 mL) was made acidic with glacial acetic acid (4.5 g, 75 mmol). In one portion, 4-thianone (44, 5.81 g, 50 mmol) was added followed by stirring at reflux for 21 h. Evaporation of the solvent gave a red oil, which was diluted with $H_2O$ (200 mL) and extracted with ether (2 × 100 mL), the latter being discarded. Basification (pH ~ 12) of the aqueous layer by the addition of NaOH pellets (3.0 g, 75 mmol) resulted in the formation of a yellow suspension which was extracted with $CH_2Cl_2$(4 × 100 mL). Combined extracts were dried ($MgSO_4$, overnight), filtered, and concentrated to afford a yellow oil which solidified upon standing. This solid was digested in 250 mL of Skelly B (bp 60°–68° C.) for 30 min, and the supernatant was decanted. Evaporation of the solvent, followed by heating the crude solid in vacuo (95°–110° C./0.3 mm Hg) in a sublimation apparatus gave a sticky white solid (mp 54°–57° C.). Recrystallization (Skelly B) afforded 4.15 g (41.6%) of white flakes of ketone (26); mp 59°–60° C. IR (KBr) $cm^{-1}$ 2965, 2935, 2900, 2875, 2805 (C—H), 1730 (C=O); $^1$H NMR (DCCl$_3$) δ1.04 (d, 6H, $CH_3$, J=6.7 Hz), 2.75–2.90 [m, 5H, ring protons, $CH(CH_3)_2$, and H(1,5)], 3.05–3.13 (m, 4H, ring protons), 3.24–3.29 (m, 2H, ring protons); $^{13}$C NMR (DCCl$_3$) ppm 18.30 (q, $CH_3$), 34.16 [t, C(2,4)], 47.52 [d, C(1,5)], 53.76 [d, $CH(CH_3)_2$], 54.16 [t, C(6,8)], 213.68 (s, C=O); $^{15}$N NMR (DCCl$_3$) ppm 39.27 [N(7)]. Anal. Calcd. for $C_{10}H_{17}NOS$: C, 60.26; H, 8.60. Found: C, 60.40; H, 8.65.

EXAMPLE XXVIII

7-Isopropyl-3-thia-7-azabicyclo[3.3.1]nonane Hydroperchlorate (8)

To a mixture of KOH pellets (85%, 3.96 g, 60 mmol) and the ketone (26, 1.0 g, 5 mmol) in triethylene glycol (25 mL) was added hydrazine (95%, 1.69 g, 50 mmol) in one portion in a 70 mL, jacketed flask equipped with a magnetic stirrer, a heating mantle, a standard condenser, a lower take-off condenser with a $N_2$ inlet, and two glass stoppers. A heating temperature of 200°–210° C. for 5 h was produced by boiling tetralin (bp 207° C.) in the jacket. After cooling to RT, the solution was diluted with chilled water (100 mL) and extracted with ether (4 × 50 mL). Combined extracts were washed with 10% NaOH (50 mL) and saturated NaCl (50 mL), dried ($Na_2SO_4$, overnight), filtered, and concentrated to a yellow oil (0.8 g). Dissolution of the oil in ether (50 mL) via magnetic stirring and cooling (5° C.) with an external ice bath was followed by dropwise addition of a solution of $HClO_4$ (60%, 1.08 g, 6.45 mmol) in isopropyl alcohol (3 mL) over 10 min. Stirring of the mixture an additional 10 min, filtering the precipitated salt, and then washing the latter with ether (~50 mL) gave an off-white solid. Dissolving the salt in hot 95% EtOH and decolorizing the solution with Norit, followed by filtering, and cooling, afforded 0.91 g (63.6%) of salt (8) as a white solid; mp 281°–282.5° C. IR (KBr) $cm^{-1}$ 3060 (N—H), 3000, 2960, 2935 (C—H), 1090 (Cl—O); $^1$H NMR (DMSO-$d_6$) δ1.28 (d, 6H, $CH_3$), 1.76 [d, 1H, H(9), J=13.3 Hz], 1.91 [d, 1H, H(9), J=12.9 Hz], 2.35 [bs, 2H, H(1,5)], 2.78 [bd, 2H, H(2,4)$_{ax}$, J=12.2 Hz], 3.14 [bd, 2H, H(2,4)$_{eq}$, J=13.6 Hz], 3.29–3.57 [m, 3H, H(6,8)$_{ax}$ and $CH(CH_3)_2$], 3.62 [d, 2H, H(6,8)$_{eq}$, J=12.7 Hz], 9.07 (bs, 1H, N—H); $^{13}$C NMR (DMSO-$d_6$) ppm 16.19 (q, $CH_3$), 25.51 [d, C(1,5)], 28.35 [t, C(9)], 30.69 [t, C(2,4)], 52.36 [t, C(6,8)], 58.66 [d, $CH(CH_3)_2$]; $^{15}$N NMR (DMSO-$d_6$) ppm 58.47 [N(7)]. Anal. Calcd. for $C_{10}H_{20}ClNO_4S$: C, 42.03; H, 7.05. Found: C, 42.10; H, 7.18.

EXAMPLE XXIX 7-(3'-Iodobenzyl)-3-thia-7-azabicyclo[3.3.1]nonan-9-one (25)

A 100 mL, three-necked, round-bottomed flask was equipped with a magnetic stirrer, a heating mantle, a standard condenser with a $N_2$ inlet, and two glass stoppers. A mixture containing 3-iodobenzylamine (1.19 g, 5.10 mmol), paraformaldehyde (1.22 g, 40.8 mmol), and $CH_3OH$ (30 mL) was made acidic with glacial acetic acid (0.46 g, 7.65 mmol). In one portion, 4-thianone (44, 0.59 g, 5.10 mmol) was added and the resulting mixture was heated under $N_2$ at reflux for 21 h. Evaporation of the solvent gave a reddish oil, which was dissolved in $H_2O$ (40 mL). Basification (pH ~ 13) of the solution by the dropwise addition of 10% NaOH resulted in the formation of a milky suspension which was extracted with ether (5 × 40 mL). Combined extracts were dried ($Na_2SO_4$, overnight), filtered, and concentrated to a yellow oil. Digestion of the oil occurred in Skelly B (125 mL, bp 60°-68° C.) for 30 min, and the supernatant was decanted. Further digestion of the residual material was effected in pentane (2×125 mL) for 30 min. Combined supernatant extracts were concentrated (rotary evaporator the vacuum pump, overnight, RT/0.2 mm Hg) to give 0.84 g (57.5%) of a slightly crude viscous oil (25) which was used without further purification in the next step. IR (film) cm$^{-1}$ 3055 (Ar C—H), 2930, 2825 (C—H), 1735 (C=O), 885, 790, 695 (C—H out of plane, meta); $^1$H NMR (DCCl$_3$) δ2.72-3.18 [m, 10H, ring protons and H(1,5)], 3.51 (s, 2H, ArCH$_2$), 7.07-7.71 (m, 4H, Ar—H); $^{13}$C NMR (DCCl$_3$) ppm 35.05 [C(2,4)], 46.95 [C(1,5)], 58.20 [C(6,8)], 60.69 (ArCH$_2$), 94.43, 127.98, 130.23, 136.44, 137.64, 140.63 (Ar—C), 213.00 (C=O).

EXAMPLE XXX 7-(3'-Iodobenzyl)-3-thia-7-azabicyclo[3.3.1]nonane Hydroperchlorate (9)

To a mixture of KOH pellets (85%, 0.48 g, 7.2 mmol) and the ketone (25, 0.224 g, 0.60 mmol) in triethylene glycol (10 mL) was added hydrazine (95%, 0.20 g, 6.0 mmol) in one portion in a 50-mL, jacketed flask equipped with a magnetic stirrer, a heating mantle, a standard condenser, a lower take-off condenser with a N$_2$ inlet, and two glass stoppers. A heating temperature of 140°-150° C. for 4 h was produced by boiling o-xylene (bp 144° C.) in the jacket. After cooling to RT, the solution was diluted with cold H$_2$O (30 mL) and was then extracted with ether (4×30 mL). Combined extracts were washed with 10% NaOH (30 mL) and saturated NaCl (30 mL), dried (Na$_2$SO$_4$, overnight), filtered, and concentrated to give a yellow oil (209 mg). Dissolution in ether (25 mL) via magnetic stirring and cooling (5° C.) in a 50-mL Erlenmeyer flask equipped with an external ice bath was followed by the dropwise addition of a solution of HClO$_4$ (60%, 0.15 g, 0.87 mmol) in isopropyl alcohol (1 mL) over 10 min. Filtration of the precipitate and then washing the latter with ether (~50 mL) gave a solid which changed to an oil. This oil was dissolved in 95% EtOH, and the solution was decolorized with Norit, filtered, and left to stand at RT overnight. White crystalline salt (9) was collected (77 mg, 27.7%); mp 169.5°-170° C. IR (KBr) cm$^{-1}$ 3045 (Ar C—H), 2950, 2915, 2825 (C—H), 1570 (C=C), 1085 (Cl—O), 780, 765 (C—H out of plane, meta); $^1$H NMR (DMSO-d$_6$) δ1.81 [m, 2H, H(9)], 2.36 [bs, 2H, H(1,5)], 2.70 [d, 2H, H(2,4)$_{ax}$, J=13.6 Hz], 3.09 [d, 2H, H(2,4)$_{eq}$, J=13.7 Hz], 3.35 [m, 2H, H(6,8)$_{ax}$], 3.58 [d, 2H, H(6,8)$_{eq}$, J=11.9 Hz], 4.22 (s, 2H, ArCH$_2$), 4.24 (s, 1H, ArCH$_2$), 7.32-8.03 (m, 4H, Ar—H), 9.20 (bs, 1H, N—H); $^{13}$C NMR (DMSO-d$_6$) ppm 25.78 [C(1,5)], 28.48 [C(9)], 30.65, [C(2,4)], 56.53 [C(6,8)], 60.04 (ArCH$_2$), 95.40, 129.93, 131.08, 132.47, 138.18, 138.93 (Ar—C); $^{15}$N NMR (DMSO-d$_6$) ppm 54.17 [N(7)]. Anal. Calcd. for C$_{14}$H$_{19}$ClINO$_4$S: C, 36.58; H, 4.17; N, 3.05; I, 27.60. Found: C, 36.87; H, 4.15; N, 2.99; I, 27.64.

EXAMPLE XXXI 3,7-Dibenzyl-3,7-diazabicyclo[3.3.1]nonan-2-one (19)

A 500-mL, three-necked, round-bottomed flask was equipped with a magnetic stirrer, a heating mantle, a standard condenser with a N$_2$ inlet, a 250-mL addition funnel, and a glass stopper. A mixture of benzylamine (10.71 g, 100 mmol), HCl (37%, 4.93 g, 50 mmol), glacial acetic acid (6.0 g, 100 mmol) and paraformaldehyde (6.31 g, 210 mmol) in CH$_3$OH (100 mL) was brought to gentle reflux with stirring under N$_2$ over 15 min. A solution of 1-benzyl-4-piperidinone (43, 18.93 g, 100 mmol) and glacial acetic acid (6.01 g, 100 mmol) in CH$_3$OH (100 mL) was then added dropwise over 1 h and this was followed by a period of reflux for an additional 18 h. Upon cooling the mixture to RT, the solvent was removed and the resulting red oil was redissolved in H$_2$O (100 mL). Combined extracts (ether, 2×100 mL) of the acidic aqueous layer were discarded. Basification of the chilled (10° C., ice water bath) water layer to pH ~ 12 was effected by the addition of 10% NaOH. Combined extracts (ether, 4×60 mL) were dried (Na$_2$SO$_4$, 1 h), filtered, and concentrated to give a viscous red oil. This oil was digested (Skelly B, 2×250 mL, 20 min), and the supernatant extracts were concentrated and then distilled (190°-215° C./10$^{-5}$ mm Hg) to give an oil. Crystallization of the oil was induced by dissolving the oil in hot pentane (800 mL) and then chilling (−10° C.) the solution to give 14.66 g (45.8%) of white, crystalline ketone (19); mp 82.5°-83.5° C. Concentration (hot plate) of the mother liquor to ~80 mL produced a second crop (0.81 g, 2.5%) of 3,7-dibenzyl-3,7-diazabicyclo[3.3.1]nonan-9-one (19); mp 81.5°-82.0° C. The total yield was (15.47 g, 48.3%).

A 70-mL, five-necked, jacketed flask was equipped with a magnetic stirrer, a heating mantle, a standard condenser, a lower take-off condenser with a N$_2$ inlet, a thermometer, and two glass stoppers. After the addition of the ketone (19, 2.0 g, 6.24 mmol), KOH pellets (85%, 4.94 g, 56.1 mmol) and hydrazine (95%, 2.11 g, 32.1 mmol) in triethylene glycol (40 mL) were added. The apparatus was flushed with N$_2$, and the mixture was heated at 140°-150° C. for 4 h using boiling o-xylene (bp 144° C.) in the jacket. Cooling the solution to RT was followed by the addition of chilled water (80 mL). Combined extracts (ether, 3×75 mL) of the suspension were washed with saturated NaCl (75 mL), dried (Na$_2$SO$_4$, overnight), filtered, and concentrated to a yellow oil (1.83 g, 95.7%) which displayed no carbonyl stretch in the IR spectrum. This oil, that is amine (37), was used without further purification.

A 100-mL, three-necked, round-bottomed flask was equipped with a magnetic stirrer, a condenser with a N$_2$ inlet, a 50-mL addition funnel, and a glass stopper. To a solution of NaIO$_4$ (2.49 g, 11.62 mmol) in H$_2$O (22.4 mL) was added RuO$_2$×H$_2$O (0.1 g) which produced a dark green solution. After the apparatus was flushed with N$_2$, a solution of the amine (37, 0.89 g, 2.9 mmol) in CCl$_4$ (16 mL) was added in one portion to produce a black mixture. The mixture was stirred at RT for 72 h and then the organic layer was separated. Further extraction of the aqueous phase was effected with CCl$_4$ (20 mL) followed by HCCl$_3$ (3×20 mL). Combined extracts were treated with isopropyl alcohol (3 mL) to destroy excess oxidant and were then filtered through a celite pad. After washing the extracts with 5% sodium thiosulfate (50 mL), the extracts were dried (Na$_2$SO$_4$, overnight), filtered, and concentrated to a yellow oil. Elution of the oil on neutral alumina (84 g, 2.4 cm×19 cm) using first ether (50 mL) and then ethyl acetate (150 mL) as eluants gave a solid material (R$_f$=0.60, ethyl acetate). This material was recrystallized by dissolving in ether (6 mL) and then refrigerating at −10° C. for 2 h; this solution was placed in a diffusion chamber of pentane for 1 h. Filtration afforded (0.27 g, 28.9%) of the lactam (17); mp 96.0°-96.5° C. IR (KBr) cm$^{-1}$ 3070, 3050, 3020 (Ar C—H), 2945, 2920, 2855, 2785, 2760 (C—H), 1645 (C=O), 1600 (C=C) 740, 710 (C—H out of plane, mono); $^1$H NMR (DCCl$_3$) δ1.69 [d, 1H, H(9), J=12.7 Hz], 1.88 [d, 1H, H(9), J=12.7 Hz], 2.05-2.09 [m, 2H, ring proton and H(1)], 2.24 (dd, 1H, ring proton, J=10.74 Hz, J'=2.66 [m, 2H, ring proton and H(5)], 3.08 [d, 1H, ring proton, J=11.8 Hz], 3.25-3.36 [m, 3H, ring proton and H(11)], 3.59 [d, 1H, H(11), J=13.2 Hz], 4.24 [d, 1H, H(10), J=14.8 Hz], 5.06 [d, 1H, H(10), J=14.7 Hz], 7.08-7.38 (m, 10H, Ar—H); $^{13}$C NMR (DCCl$_3$) ppm 27.94 [C(9)], 28.07 [C(5)], 39.07 [C(1)], 49.84 [C(10)], 51.60 [C(4)], 57.07 [C(8)], 59.03 [C(6)], 62.70 [C(11)], 126.88, 127.14, 128.17, 128.40, 128.49, 128.72, 137.39, 138.13 (Ar—C), 172.77 (C=O). Anal. Calcd. for C$_{21}$H$_{24}$N$_2$O: C, 78.72; H, 7.55. Found: C, 78.39; H, 7.78.

EXAMPLE XXXII

7-Benzyl-9,9-dimethoxy-3-thia-7-azabicyclo[3.3.1]-nonane Hydroperchlorate (11)

Caution: The use of shields, protective goggles and gloves is very strongly recommended when performing this experiment. The formation of explosive methyl perchlorate is a likely side reaction in this experiment. No difficulty was noted when the reaction was performed as described, but this may have been fortuitous. A one-necked, 100-mL, round-bottomed flask was fitted with a Soxhlet containing 3A molecular sieves (30 g), a condenser, a heating mantle, a magnetic stirrer, and a heating mantle. The effective cycling volume of the Soxhlet was approximately 15 mL. The flask was charged with a solution of the ketone (18, 1.0 g, 4 mmol) in methanol (20 mL) and benzene (20 mL). To this solution was added HClO$_4$ (60%, 2.0 g, 12 mmol) in one portion. The apparatus was flushed with N$_2$ and the pale yellow solution was heated at reflux with stirring and cycling through the Soxhlet for 24 h. The solution was cooled to RT and concentrated to about 5 mL. Ethyl ether (20 mL) was added, thus precipitating the salt as a powder. This was filtered, washed with ether (5 mL), and dissolved in hot methanol (20 mL, decolorizing carbon). Trituration with ether (25 mL), followed by standing for 24 h, afforded the salt (11) (0.74 g, 46.2%) as small white crystals; mp 193°-194° C. (dec); IR (KBr) cm$^{-1}$ 2800-2600 (N—H), 1090 (Cl—O); $^1$H NMR (DMSO-d$_6$) δ2.58 [bs, 2H, H(1,5)], 2.75 [d, 2H, H(2,4)$_{ax}$, J=14 Hz], 3.15-3.18 [m, 8H, H(2,4)$_{eq}$ and OCH$_3$], 3.38 [dd, or bt, 2H, H(6,8)$_{ax}$, J=12 Hz], 3.60 [d, 2H, H(6,8)$_{eq}$, J=12 Hz], 4.33 (d, 2H, CH$_2$Ph, J=5 Hz), 7.49-7.62 (m, 5H, Ar—H); $^{13}$C NMR (DMOS-d$_6$) ppm 28.8 [t, C(2,4)], 32.2 [d, C(1,5)], 46.6 (q, OCH$_3$), 47.0 (q, OCH$_3$), 54.5 [t, C(6,8)], 60.2 (t, CH$_2$Ph), 95.1 [s, C(9)], 129.0, 129.5, 130.1, 130.2 (d, Ar—C); $^{15}$N NMR (DMSO-d$_6$) ppm 53.5 [N(7)]. Anal. Calcd. for C$_{26}$H$_{24}$ClNO$_6$S: C, 48.79; H, 6.14; Cl, 9.00; N, 3.56; S, 8.14. Found: C, 48.73; H, 6.09; Cl, 9.39; N, 3.54; S, 8.40.

EXAMPLE XXXIII

3,7-Dibenzyl-9,9-dimethoxy-3,7-diazabicyclo[3.3.1]nonane Hydroperchlorate (12)

Caution: The use of shields, protective goggles and gloves is very strongly recommended when performing this reaction. The formation of explosive methyl perchlorate is a likely side reaction in this experiment. No difficulty was noted when the experiment was performed as described, but this may have been fortuitous. A one-necked, 100-mL, round-bottomed flask was equipped with a Soxhlet containing 3A molecular sieve (30 g), a condenser with a N$_2$ inlet, a magnetic stirrer, and a heating mantle. The effective cycling volume of the Soxhlet was approximately 20 mL. The flask was charged with a solution of the ketone (19, 1.0 g, 3.12 mmol) in CH$_3$OH (25 mL) and benzene (25 mL) to which was added HClO$_4$ (60%, 1.5 g, 8.96 mmol) in one portion. The apparatus was flushed with N$_2$ and the colorless solution was heated to reflux with cycling through the Soxhlet. After 24 h, the now pale yellow solution was cooled to RT and concentrated to a white solid which was filtered, washed with C$_6$H$_6$ (10 mL), and recrystallized (CH$_3$OH, 80 mL) to afford the monoperchlorate (0.91 g) as small white crystals, mp 223.6°-224.0° C. (dec). The mother liquor was concentrated to approximately 10 mL. Upon cooling to a −10° C. overnight, a second crop of salt (12) was obtained (89.4 mg, 68.6% total), mp 219°-220° C. (dec). The spectral data were as follows: IR (KBr) cm$^{-1}$ 2800-2600 (N-H), 1100 (Cl—O); $^1$H NMR (DMSO-d$_6$) δ2.35 [bs, 2H, H(1,5)], 2.90 [d, 4H, H(2,4,6,8)$_{ax}$, J=13 Hz], 3.08 [d, 4H, H(2,4,6,8)$_{eq}$, J=13 Hz], 3.14 (s, 6H, OCH$_3$), 3.88 (s, 4H, CH$_2$Ph), 7.38-7.54 (m, 10H, Ar—H), 9.84 (bs, 1H, N-H); $^{13}$C NMR (DMSO-d$_6$) ppm 33.0 [d, C(1,5)], 47.0 (q, OCH$_3$), 53.8 [t, C(2,4,6,8)], 59.6 (t, CH$_2$Ph), 95.4 [C(9)], 128.2, 128.4, 129.6, 133.5 (Ar—C); $^{15}$N NMR (DMSO-d$_6$) ppm 52.9 [N(3,7)]. Anal. Calcd. for C$_{23}$H$_{31}$ClN$_2$O$_6$: C, 59.16; H, 6.69; Cl, 7.59; N, 6.00. Found: C, 58.98; H, 6.81; Cl, 7.86; N, 6.28.

EXAMPLE XXXIV

7-Benzyl-3-thia-7-azabicyclo[3.3.1]nonane 3-Oxide (49)

A 200-mL flask was equipped with a magnetic stirrer, an ice bath, and a condenser with nitrogen inlet. To a stirred, chilled (5° C.) solution of the amine (27, 1.4 g, 6 mmol) in methanol (60 mL) was added dropwise a solution of NaIO$_4$ (1.35 g, 6.3 mmol) in water (15 mL) over 30 min. After stirring for one hour, the suspension was filtered and washed with methanol (50 mL); the washings and filtrate were combined and concentrated to a residue which was partitioned between H$_2$CCl$_2$ and water (40 mL each). Additional extracts (HCCl$_3$, 3×40 mL) of the aqueous layer were combined with the initial extract, and the solution was dried (Na$_2$SO$_4$) and concentrated to afford an oil which solidified upon standing. Recrystallization (HCCl$_3$/pentane) of the solid gave 1.15 g (76.9%) of crystalline (49); mp 140°-141° C. IR (KBr) cm$^{-1}$ 3085, 3065, 3030, 2955, 2920, 2895, 2815, 1495, 1020, 740, 705; $^1$H NMR (DCCl$_3$) δ1.59 [bd, 1H, H(9), J=13.3 Hz], 1.86 [bd, 1H, H(9), J=13.2 Hz], 2.20 [d, 2H, H(2,4)$_{ax}$, J=11.7 Hz], 2.37 bs, 2H, H(1,5)], 2.62 [d, 2H, H(6,8)$_{ax}$, J=12.0 Hz], 2.78 [d, 2H, H(2,4)$_{eq}$, J=11.8 Hz], 3.51 [d, 2H, H(6,8)$_{eq}$, J=11.7 Hz], 3.55 [s, 2H, ArCH$_2$], 7.26-7.39 (m, 5H, Ar—H); $^{13}$C NMR (DCCl$_3$) ppm 31.86 [t, C(9)], 32.59 [d, C(1,5)], 57.42 [t, C(2,4)], 58.59 [C(6,8)], 62.88 (ArCH$_2$), 127.20, 128.39, 129.12, 137.67; $^{15}$N NMR (DCCl$_3$) ppm 49.37 [N(7)]. Anal. Calcd. for C$_{14}$H$_{19}$NOS: C, 67.43; H, 7.68. Found: C, 67.61; H, 7.73.

EXAMPLE XXXV

7-Benzyl-3-thia-7-azabicyclo[3.3.1]nonane 3-Oxide Hydroperchlorate (10)

A 50-mL Erlenmeyer flask was equipped with a magnetic stirrer and an ice bath. To a stirred, chilled (5° C.) solution of the sulfoxide (49, 0.47 g, 1.88 mmol) in ether (20 mL) and isopropyl alcohol (3 mL) was added dropwise a solution of HClO$_4$ (60%, 0.63 g, 3.75 mmol) in isopropyl alcohol (3 mL) over 30 min. Filtering of the precipitate followed, and latter was washed with ether (50 mL) and then recrystallized (95% ethanol) to give a crystalline salt (10) (0.51 g, 78.1%); mp 137°-138° C. IR (KBr) cm$^{-1}$ 3090, 2970, 2950, 1465, 1095, 745, 705; $^1$H NMR (D$_3$COD) δ1.70 [bd, 1H, H(9), J=14.0 Hz], 2.01 [bd, 1H, H(9), J=13.9 Hz], 2.61 [bd, 2H, H(2,4)$_{ax}$, J=11.8 Hz], 2.69 [bs, 2H, H(1,5)], 3.06 [bd, 2H, H(2,4)$_{eq}$, J=11.8 Hz], 3.36 [bd, 2H, H(6,8)$_{ax}$, J=13.1 Hz], 3.94 (s, 2H, ArCH$_2$), 4.19 [bd, 2H, H(6,8)$_{eq}$, J=12.9 Hz], 7.35-7.42 (m, 5H, Ar—H); $^{13}$C NMR (D$_3$COD) ppm 30.80 [C(9)], 36.27 [C(1,5)], 53.94 [C(2,4)], 58.56 [C(6,8)], 61.07 [ArCH$_2$], 129.43 129.78, 131.49, 135.29; $^{15}$N NMR (DMSO-d$_6$) ppm 56.45 [N(7)]. Anal. Calcd. for C$_{14}$H$_{20}$ClNSO$_5$: C, 48.06; H, 5.76. Found: C, 47.84; H, 5.74.

EXAMPLE XXXVI

7-Benzyl-3-thia-7-azabicyclo[3.3.1]nonan-9-one
6,8,10—$^{14}$C$_3$ (18)*

Caution: Special precautions should be taken when handling radioactive chemicals. All reactions should be carried out in a well ventilated hood with protective shields to prevent possible contamination of the lab area. Protective safety goggles as well as quality rubber gloves should also be worn at all times since exposure to the $^{14}$C materials could be dangerous. A 50-mL, three-necked, round-bottomed flask was equipped with a magnetic stirrer, a heating mantle, a condenser with a N$_2$ inlet, and two glass stoppers. To a mixture containing benzylamine (0.43 g, 4 mmol), [$^{14}$C] benzylamine HCl [1 mg, 7×10$^{-3}$ mmol, 0.5 mCi (minimum activity, ICN)] in H$_2$O (2.5 mL), and deoxygenated methanol (15 mL) was added HCl (37%, 0.1 g, 1 mmol) followed by glacial acetic acid (0.36 g, 6 mmol). Addition in one portion of paraformaldehyde (0.96 g, 32 mmol) and [$^{14}$C] paraformaldehyde [1 mg, 3.3×10$^{-2}$ mmol, 0.5 mCi (minimum activity, ICN)] was followed by subsequent addition of 4-thianone (43, 0.47 g, 4 mmol) all at once with stirring. After the mixture was heated at reflux under N$_2$ for 6 h, the solution was concentrated to 2-3 mL and then diluted with H$_2$O (30 mL). The aqueous solution was extracted with ether (2×30 mL), and the latter was discarded. Chilling (via ice water bath) of the aqueous layer to below 5° C. was followed by basification (pH~12) with NaOH pellets (97%, 0.29 g, 7 mmol) which resulted in the formation of a cloudy suspension. Combined extracts (ether, 4×30 mL) were dried (Na$_2$SO$_4$, overnight), filtered, and concentrated (rotary evaporator) to give a viscous oil, which was then digested in 200 mL of Skelly B (bp 60°-68° C.) for 0.5 h. Concentration of the supernatant afforded a yellow oil which was subjected to heating at high vacuum (110° C./0.1 mm Hg) in a sublimation apparatus to give 0.13 g of ketone (18)*; mp 91°-93° C. The residue which remained was again dissolved in ether (~50 mL), and the latter solution was dried (Na$_2$SO$_4$, overnight), filtered, and concentrated to an oil. Digestion of the oil was effected in 50 mL of Skelly B for 0.5 h, and the supernatant was concentrated to a viscous oil. This material was heated under vacuum (110° C./0.1 mm Hg) in a sublimation apparatus and gave 0.05 g of slightly crude ketone (18)*; mp 78°-80° C. A mixture melting point determination with the first crop was 86°-88° C. without significant depression. This gave a total yield of 0.18 g (17.7%) of ketone (18)* which was used without further purification in the next step.

EXAMPLE XXXVII

7-Benzyl-3-thia-7-azabicyclo[3.3.1]nonane
Hydroperchlorate 6,8,10—$^{14}$C$_3$ (48)*

Caution: Special precautions should be taken when handling radioactive chemicals. All reactions should be carried out in a well ventilated hood with protective shields to prevent possible contamination of the lab area. Protective safety goggles as well as quality rubber gloves should also be worn at all times since exposure to the $^{14}$C materials could be dangerous. To a mixture of KOH pellets (85%, 0.48 g, 8.5 mmol) and the ketone (18)* (0.18 g, 0.71 mmol) in triethylene glycol (5 mL) was added hydrazine (95%, 0.23 g, 7.1 mmol) in one portion in a 50-mL, jacketed flask equipped with a magnetic stirrer, a condenser, a lower take-off condenser and two glass stoppers. A heating temperature of 140°-150° C. for 4 h was produced by boiling o-xylene (bp 144° C.) in the jacket. After cooling to RT, the solution was diluted with chilled H$_2$O (30 mL) and extracted with ether (4×20 mL). Combined extracts were dried (Na$_2$SO$_4$, overnight) and filtered. Cooling of the ethereal solution to below 5° C. was followed by the dropwise addition of HClO$_4$ (60%, 1 mL) over 10 min with stirring, which resulted in the formation of a white precipitate. Crude salt (48)* was filtered, recrystallized (95% EtOH), and dried over P$_2$O$_5$ (78° C./0.1 mm Hg) to give 0.14 g (58.6%) of white crystals of salt (48)*; mp 154.5°-155.0° C.; (lit 155°-156° C.). A stock solution (3.49 mg/mL) of salt (48)* was prepared using DMSO, H$_2$O, and 0.1N HCl (40:53.5:6.5 by volume). Samples were made by diluting 4 μL of the stock solution with 10 mL of Aquasol 2 scintillation cocktail (New England Nuclear Research Products). Measurements of activity were obtained at room temperature using a TRI-CARB liquid scintillation analyzer, model 1900 CA (Packard Instrument Company). An average count of 19,800 DPM was observed for each sample and the specific activity was determined to be 0.64 μCi/mg. In similar fashion, samples were prepared from stock solution of the salt (48)* in methanol and the specific activity was determined to be 0.63 μCi/mg.

To illustrate the useful biological properties of the compounds described in this invention, selected derivatives were screened for antiarrhythmic activity using dog models. The clinically used agent lidocaine and 7-benzyl-3-thia-7-azabicyclo[3.3.1]nonane hydroperchlorate (48) [U.S. Pat. No. 4,581,361] were employed as standards as basis for comparison. A small infarction was created in an area of the dog heart and thereafter electrical pacing was initiated to generate a sustained ventricular tachycardia (VT). This irregular beating pattern of the heart results in a reduction of the pumping capability of the heart in a manner now accepted as resembling symptoms observed in humans during a heart attack (see: Scherlag, B. J. et. al., Am. J. Cardiol. 1983, 51, 207; Bailey, B. R. et. al., J. Med. Chem. 1984, 27, 759; Thompson, M. D. et. al., J. Med. Chem. 1987, 30, 780; U.S. Pat. No. 4,581,361; and U.S. Pat. No. 4,778,892 for further details, said references incorporated herein for such purposes). The effects of the selected compounds in terms of ability to reduce the rate of the induced VT or to eliminate the same (abolish the VT completely or at least not allow it to be sustained) is then evaluated and compared to lidocaine or to 7-benzyl-3-thia-7-azabicyclo[3.3.1]nonane hydroperchlorate (48). Since the latter hydroperchlorate proved superior to lidocaine in most of the studies, data in Table A are compared to that obtained for the salt (48) cited herein. In Table A, it is clear that salts (1), (3), (5), (11), (13), and (14) are extremely effective in eliminating the induced VT as was the standard 7-benzyl-3-thia-7-azabicyclo[3.3.1]nonane hydroperchlorate (48) at 3 mg/kg as well as at 6 mg/kg. Salts (10), (12), (15), and (17) reduced the rates of the induced VT but did not abolish them. In contrast, salt (8) exhibited little effect on the dog model which suggests there exists a high degree of specificity of action of these molecules in terms of antiarrhythmic activity. Thus, these heterocyclic molecules claimed in this application have electrocardiology properties equal or superior to those of the standard 7-benzyl-3-thia-7-azabicyclo[3.3.1]nonane hydroperchlorate (48) which is known to have such superior properties to those of lidocaine (see: U.S. Pat. Nos. 4,581,361 and 4,778,891) which is a clinically used agent for the treatment of victims of heart attacks.

In principle, it is felt that the compositions of the present invention can be employed separately or incombination with each other or in combination with other drugs to achieve either individually or in combination the desired antiarrhythmic properties. It is expected that the composition can be utilized and administered via a variety of methods including by way of an example, but not limited thereto, intravenously, orally, by suppository, by inhalation, and the like. Furthermore, it is generally felt that the compositions as claimed either specifically possess antiarrhythmic activity or generally are broad biologically active or the respective compositions are intermediates to antiarrhythmic and biologically active species that are released or created in situ as the result of administration of the drug.

above compounds. The techniques employed in these preliminary studies are well documented, but a summary of pharmacokinetic procedures can be found in: J. D. Baggot, "Principals of Drug Disposition in Domestic Animals: The Basis of Veterinary Clinical Pharmacology", W. B. Saunders Company, Philadelphia, 1977. These studies were conducted using $^{14}$C-labelled (48)* [Prepared by the method of Zisman, Berlin, et al. *J. Labelled Compounds and Radiopharmaceuticals*, In Press (1989)] in Sprague-Dawley rats.

Radioactivity-time data obtained by analysis of blood samples collected after intracardiac or oral administration are recorded in Tables B and C so designated. Coefficients and exponents of the disposition curves which best described changes in blood radioactivity with time after administration were obtained using a microcomputer program [R. D. Brown et al. *J. Pharmaceutical Sciences*, 67, 1687 (1978)]. The disposition of (48)* after intracardiac administration was well described by a two-compartment open model and the pharmacokinetic parameters derived from the analysis of individual blood radioactivity data are presented in Table D so designated. The median half-life of elimination ($T_{\frac{1}{2}(\beta)}$) of radioactivity was 5.7 hours, which suggested that a moderate to reasonably long dosage interval might be appropriate for therapeutic use. The median apparent volume of distribution, based on total area under the disposition curve ($V_{d(area)}$), was high (4070 ml/kg) indicating extensive distribution into body tissues. The high total body clearance value ($Cl_B = 470$) confirms the presence of efficient drug elmination pathways.

Pharmacokinetic terms describing changes in blood radioactivity after oral administration are presented in

TABLE A
ANTIARRHYTHMIC PROPERTIES OF REPRESENTATIVE 3-AZABICYCLO[3.3.1]NONANE SALTS

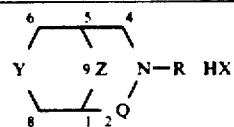

| Comp[a] | R | Y | Z | (Effect on SVT[b]) 3mg/kg | 6mg/kg |
|---|---|---|---|---|---|
| (1) | CH(CH$_3$)$_2$ | NC(O)Ph | CH$_2$ | NSVT | NSVT |
| (3) | CH(CH$_3$)$_2$ | NCH$_2$C$_6$H$_4$-3,4(OCH$_3$)$_2$ | CH$_2$ | NSVT | NSVT |
| (5) | CH(CH$_3$)$_2$ | NCH$_2$Ph | CH$_2$ | NSVT | NSVT |
| (8) | CH(CH$_3$)$_2$ | S | CH$_2$ | No action | No action |
| (Stand.-48) | CH$_2$Ph | S | CH$_2$ | NSVT[c] | NSVT |
| (10) | CH$_2$Ph | S⟶O | CH$_2$ | Reduced rate of VT | Reduced rate of VT |
| (11) | CH$_2$Ph | S | C(OCH$_3$)$_2$ | NSVT | NSVT |
| (12) | CH$_2$Ph | NCH$_2$Ph | C(OCH$_3$)$_2$ | Reduced rate of VT | Reduced rate of VT |
| (13) | CH$_2$PH | CHCO$_2$Et | CH$_2$ | NSVT | NSVT |
| (14) | CH$_2$Ph | CHCO$_2$Et | C(SCH$_2$)$_2$ | NSVT | NSVT |
| (15) | NC(O)Ph | S | CH$_2$ | Reduced rate of VT | Reduced rate of VT |
| (17)[d] | CH$_2$Ph | NCH$_2$Ph | CH$_2$ | Reduced rate of VT | Reduced rate of VT |

[a]X = ClO$_4$, Cl, Br, citrate, fumarate, HSO$_4$
[b]SVT = Sustained ventricular tachycardia induced by electrical pacing of infarcted dog heart
[c]NSVT = Nonsustained ventricular tachycardia (or abolished ventricular tachycardia)
[d]All compounds have Q is CH$_2$ except (17) where Q is C=O In order to determine the potential viability of members of the above family to act as useful antiarrhythmic agents in vivo, a pharmacokinetic and metabolism study was undertaken using a representative example from the Table D so designated. Compartmental analysis showed that the data fitted a one-compartment pharmacokinetic model. Oral dosing resulted in rapid and extensive absorption and peak concentrations within 30 minutes after administration. The ratio of the areas under the radioactivity-time curves obtained after oral and intracardiac administration ($AUC_{po}/AUC_{ic}$) indicates a high bioavailability ($\pm 81\%$). Thus, the oral route of administration may be suitable for therapeutic management of patients suffering from cardiac arrhythmias.

TABLE B

Kinetics of appearance of radioactivity [dpm/ml] in blood after intracardiac administration of a bolus dosage (10 mg/kg) of (48)*(1332000dpm/mg).

| Time after administration (hours) | Individual rats | | | | | | | Mean | SD |
|---|---|---|---|---|---|---|---|---|---|
| | #2 | #3 | #8 | #9 | #10 | #15 | #16 | | |
| 0.0333 | — | 6802 | 6732 | 6419 | 6173 | 6595 | 7140 | 6644 | 333 |
| 0.0833 | 5482 | 5424 | — | 5496 | 5661 | 6106 | 7262 | 5905 | 710 |
| 0.1667 | 4741 | 5520 | 6087 | 4903 | 4780 | 5752 | 6435 | 5460 | 674 |
| 0.3333 | 4807 | 4225 | — | 4261 | 4768 | 5219 | 6197 | 4913 | 731 |
| 0.5 | — | 5294 | 3233 | 4210 | 4228 | 5152 | 3938 | 4343 | 773 |
| 1 | 2911 | 3619 | 4182 | 4343 | 3002 | 3433 | 3873 | 3623 | 551 |
| 2 | 1862 | 2004 | 2495 | 2451 | 2721 | 2463 | 1907 | 2272 | 340 |
| 3 | — | 1307 | 2357 | 2369 | 2314 | — | — | 2087 | 520 |
| 4 | 1374 | 1382 | 2316 | 2429 | 2379 | 1578 | 1438 | 1842 | 504 |
| 6 | — | 1719 | 2089 | 1905 | 2186 | 1690 | 1377 | 1828 | 295 |
| 10 | 1005 | 1113 | 1123 | 1191 | 903 | 1040 | 900 | 1039 | 112 |
| 16 | — | 534 | 332 | 515 | 353 | 395 | 349 | 413 | 89 |
| 24 | 242 | 308 | 71 | 60 | 178 | 197 | 144 | 171 | 89 |

TABLE C

Kinetics of appearance of radioactivity [dpm/ml] in blood after oral administration of a bolus dosage (10 mg/kg) of (48)*(1332000dpm/mg).

| Time after administration (hours) | Individual rats | | | | | | Mean | SD |
|---|---|---|---|---|---|---|---|---|
| | #4 | #6 | #7 | #11 | #12 | #13 | | |
| 0.1667 | 1928 | 802 | 1026 | 1601 | 479 | 967 | 1134 | 534 |
| 0.3333 | 2153 | 1723 | 2311 | 3265 | 754 | 1946 | 2025 | 818 |
| 0.5 | 4281 | 2086 | 2659 | 4421 | 1025 | 2151 | 2771 | 1335 |
| 1 | 3895 | 1911 | 2272 | 3154 | 958 | 2106 | 2383 | 1022 |
| 2 | 2208 | 1545 | 1618 | 2896 | 991 | 2043 | 1884 | 654 |
| 4 | 1786 | 2034 | 2114 | 2017 | 1767 | 1713 | 1905 | 169 |
| 6 | 1601 | 1502 | 1224 | 1594 | 1714 | 1138 | 1462 | 230 |
| 10 | 893 | 662 | 885 | 1118 | 1613 | 984 | 1026 | 324 |
| 16 | 418 | 245 | 302 | 140 | 586 | 390 | 347 | 154 |
| 24 | 300 | 89 | 79 | 66 | 197 | 75 | 134 | 95 |

TABLE D

Pharmacokinetic values derived from each rat's (48)* blood disposition curves.

I. Intracardiac administration:

| Determinant | Individual rats | | | | | | | Mean | SD |
|---|---|---|---|---|---|---|---|---|---|
| | 2 | 3 | 8 | 9 | 10 | 15 | 16 | | |
| A (dpm/ml) | 3670 | 3924 | 2583 | 2532 | 2350 | 3852 | 5097 | 3330 | 966 |
| B (dpm/ml) | 2192 | 2152 | 4333 | 4647 | 3659 | 2972 | 2652 | 1616 | 1808 |
| $\alpha$ (hr$^{-1}$) | 1.36 | 0.86 | 1.93 | 11.49 | 2.18 | 1.48 | 1.62 | 1.55 | 2.96 |
| $\beta$ (hr$^{-1}$) | 0.090 | 0.080 | 0.163 | 0.164 | 0.131 | 0.115 | 0.121 | 0.124 | 0.035 |
| $K_{21}$ (hr$^{-1}$) | 0.568 | 0.359 | 1.276 | 7.499 | 1.380 | 0.710 | 0.636 | 1.775 | 2.551 |
| $K_{el}$ (hr$^{-1}$) | 0.217 | 0.194 | 0.248 | 0.252 | 0.207 | 0.241 | 0.310 | 0.238 | 0.038 |
| $K_{12}$ (hr$^{-1}$) | 0.673 | 0.394 | 0.578 | 3.908 | 0.726 | 0.646 | 0.800 | 1.103 | 1.243 |
| $t_{\frac{1}{2}(\beta)}$ (hr) | 7.67 | 8.60 | 4.23 | 4.20 | 5.28 | 5.99 | 5.70* | | |
| $t_{\frac{1}{2}(\alpha)}$ (hr) | 0.50 | 0.79 | 0.35 | 0.06 | 0.31 | 0.46 | 0.42* | | |
| $C_o$ (dpm/ml) | 5863 | 6077 | 6917 | 7179 | 6010 | 6824 | 7750 | 6660 | 701 |
| $V_c$ (ml/kg) | 2271 | 2191 | 1925 | 1855 | 2216 | 1951* | 1718 | | |
| $V_{d(area)}$ (ml/kg) | 5471 | 5291 | 2926 | 2843 | 3504 | 4070* | 4390 | | |
| $V_{d(ss)}$ (ml/kg) | 4963 | 4596 | 2798 | 2822 | 3381 | 3725* | 3879 | | |
| $Cl_B$ (ml/hr·kg) | 494 | 426 | 478 | 468 | 459 | 470* | 533 | | |
| $AUC_{ic}$ | 25282 | 27480 | 29169 | 30489 | 28444 | 27126 | 24104 | 27442 | 2205 |

I. Oral administration:

| Determinant | Individual rats | | | | | | Mean | SD |
|---|---|---|---|---|---|---|---|---|
| | 4 | 6 | 7 | 11 | 12 | 13 | | |
| $\beta$ (hr$^{-1}$) | 0.107 | 0.138 | 0.143 | 0.181 | 0.149 | 0.137 | 0.143 | 0.023 |
| $t_{\frac{1}{2}(\beta)}$ (hr) | 6.42 | 5.00 | 4.81 | 3.80 | 4.63 | 5.04 | 4.90* | |
| $AUC_{po}$ | 25306 | 18755 | 20243 | 24510 | 24383 | 20555 | 22292 | 2760 |
| $AUC_{po}/AUC_{ic}$ | | | | | | | 0.81233 | |

*Values represent medians

Tissue distribution of (48)* was studied by measuring the radioactivity in selected organs collected from rats sacrificed at several time intervals after oral administration. Data obtained from these studies is reported in Table E so designated. High levels of radioactivity were measured in liver and kidney which is consistent with the extensive metabolism and excretion of metabolites commonly encountered with highly lipid soluble xenobiotics [agent (48)* has both polar and nonpolar structural features]. These observations correlate well with the high volume of distribution calculated from pharmacokinetic data. Reasonably high concentrations of radioactivity in the heart confirm that (48)* achieves good penetration into the target organ. Radioactivity in the brain and perirenal fat were low in comparison with other tissues and decreased steadily with time after administration. This suggests that central neurotoxicity may not limit the therapeutic use of these agents and that long-term accumulation in fat depots may not present a toxicological hazard.

Thin layer chromatographic analysis of urine samples collected after oral administration of $^{14}$C-labelled (48)* to rats indicated that most of the dose was excreted in the form of metabolites. Using mass spectrometry, the major metabolite was identified as $^{14}$C-labelled (15)*, the structure of which was confirmed by comparison with an authenticated sample of unlabelled (15). Consequently, amide (15) is an active metabolite of (48) and is therefore a potentially viable agent in its own right.

TABLE E

Concentration of radioactivity in selected organs and tissues after oral administration of a bolus dosage (10 mg/kg) of (48)*(1332000dpm/mg).

| Time after administration (hr) | Experimental units | | | Mean | SD |
|---|---|---|---|---|---|
| | I | II | III | | |
| 1. Blood concentrations (dpm/ml): | | | | | |
| 0.083 | 2330 | 1970 | 3975 | 2758 | 1069 |
| 0.25 | 5170 | 6755 | 4615 | 5513 | 1111 |
| 0.5 | 6020 | 6010 | 4935 | 5655 | 624 |
| 0.75 | 4370 | 3335 | 4245 | 3983 | 565 |
| 1.5 | 2840 | 2790 | 3300 | 2977 | 281 |
| 4 | 2060 | 2580 | 1800 | 2147 | 397 |
| 8 | 740 | 650 | 740 | 710 | 52 |
| 16 | 276 | 219 | 295 | 263 | 40 |
| 1. Kidney concentrations (dpm/g): | | | | | |
| 0.083 | 11320 | 5425 | 21341 | 12695 | 8047 |
| 0.25 | 27222 | 34142 | 20528 | 27297 | 6807 |
| 0.5 | 31622 | 39516 | 28700 | 33279 | 5595 |
| 0.75 | 26793 | 19249 | 24987 | 23676 | 3939 |
| 1.5 | 18881 | 16254 | 21566 | 18900 | 2656 |
| 4 | 15219 | 17715 | 12217 | 15050 | 2753 |
| 8 | 4963 | 4835 | 5296 | 5031 | 238 |
| 16 | 2591 | 1761 | 2285 | 2212 | 420 |
| 24 | 1250 | 2489 | 1004 | 1581 | 796 |
| 1. Liver concentrations (dpm/g): | | | | | |
| 0.083 | 49025 | 37302 | 33768 | 40032 | 7986 |
| 0.25 | 77479 | 86705 | 53662 | 72615 | 17050 |
| 0.5 | 82327 | 81324 | 68846 | 77499 | 7510 |
| 0.75 | 40648 | 16117 | 46449 | 34405 | 16101 |
| 1.5 | 14156 | 18970 | 21791 | 18306 | 3861 |
| 4 | 14430 | 17811 | 15814 | 16018 | 1700 |
| 8 | 10272 | 9195 | 9855 | 9774 | 543 |
| 16 | 6886 | 4065 | 4948 | 5300 | 1443 |
| 24 | 3427 | 4709 | 2563 | 3566 | 1080 |
| 1. Heart concentrations (dpm/g): | | | | | |
| 0.083 | 4813 | 1236 | 4292 | 3447 | 1932 |
| 0.25 | 5402 | 5647 | 3890 | 4980 | 952 |
| 0.5 | 5071 | 4903 | 4107 | 4694 | 515 |
| 0.75 | 3442 | 2785 | 3608 | 3278 | 435 |
| 1.5 | 2415 | 2511 | 2736 | 2554 | 165 |
| 4 | 1820 | 2114 | 1676 | 1870 | 223 |
| 8 | 826 | 668 | 790 | 761 | 83 |
| 16 | 336 | 273 | 412 | 340 | 70 |
| 24 | 221 | 320 | 184 | 242 | 70 |
| Perirenal fat concentrations (dpm/g): | | | | | |
| 0.083 | 2583 | 647 | 4670 | 2633 | 2012 |
| 0.25 | 16771 | 1925 | 926 | 6541 | 8874 |

TABLE E-continued

Concentration of radioactivity in selected organs and tissues after oral administration of a bolus dosage (10 mg/kg) of (48)*(1332000dpm/mg).

| Time after administration (hr) | Experimental units | | | Mean | SD |
|---|---|---|---|---|---|
| | I | II | III | | |
| 0.5 | 1606 | 2068 | 2145 | 1940 | 292 |
| 0.75 | 1070 | 1866 | 2599 | 1845 | 765 |
| 1.5 | 718 | 933 | 745 | 799 | 117 |
| 4 | 610 | 508 | 562 | 560 | 51 |
| 8 | 577 | 172 | 558 | 436 | 229 |
| 16 | 216 | 138 | 271 | 208 | 67 |
| 24 | 77 | 119 | 97 | 98 | 21 |
| 1. Brain concentrations (dpm/g): | | | | | |
| 0.083 | 1280 | 296 | 1496 | 1024 | 640 |
| 0.25 | 1562 | 1980 | 1028 | 1523 | 477 |
| 0.5 | 824 | 971 | 643 | 813 | 164 |
| 0.75 | 711 | 1051 | 551 | 771 | 255 |
| 1.5 | 477 | 506 | 626 | 536 | 79 |
| 4 | 399 | 343 | 399 | 380 | 32 |
| 8 | 248 | 232 | 274 | 251 | 21 |
| 16 | 108 | 106 | 92 | 102 | 9 |
| 24 | 70 | 96 | 79 | 82 | 13 |

The 3-azabicyclo[3.3.1]nonane compounds described herein may be generally characterized by the formula:

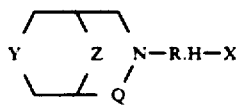

wherein
H-X represents a pharmacologically acceptable acid,
Q represents $CH_2$, or CO,
Z represents $CH_2$, CO, $C(OCH_3)_2$, or

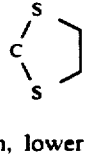

R represents hydrogen, lower alkyl, or a benzyl- or benzoyl group wherein the phenyl ring is unsubstituted or is substituted by halogen or by 1 to 3 methoxy groups, a benzene sulfonyl group, or

and
Y represents S, S→O, CH—$CO_2C_2H_5$, or a group N—R' wherein R' is lower alkyl or a benzyl- or benzoyl group, in which group the phenyl ring is unsubstituted or is substituted by halogen or by 1 to 3 methoxy groups.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A 3-azabicyclo [3.3.1]nonane compound having the following formula:

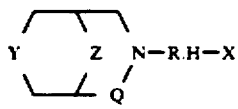

wherein

H-X represents a pharmacologically acceptable acid,
Q represents $CH_2$, or CO,
Z represents $CH_2$, CO, $C(OCH_3)_2$, or

R represents hydrogen, lower alkyl, or a benzyl- or benzoyl group wherein the phenyl ring is unsubstituted or is substituted by halogen or by 1 to 3 methoxy groups, a benzene sulfonyl group, or $$C\begin{array}{c}S\\ \\S\end{array}\Big)$$

and
Y represents S→O.

2. A compound according to claim 1 wherein Q represents $CH_2$.

3. A compound according to claim 1 wherein Z represents $CH_2$.

4. A compound according to claim 1 wherein R represents $C_1$-$C_4$-alkyl or an optionally substituted benzyl- or benzoyl group.

* * * * *